US010335578B2

United States Patent
Ishida

(10) Patent No.: US 10,335,578 B2
(45) Date of Patent: Jul. 2, 2019

(54) CATHETER ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/296,683

(22) Filed: Oct. 18, 2016

(65) Prior Publication Data

US 2017/0043132 A1    Feb. 16, 2017

Related U.S. Application Data

(63) Continuation of application No. PCT/JP2016/063914, filed on May 10, 2016.

(30) Foreign Application Priority Data

May 15, 2015 (JP) ................. 2015-100357

(51) Int. Cl.
*A61M 25/06* (2006.01)
*A61M 25/01* (2006.01)

(52) U.S. Cl.
CPC .... *A61M 25/0606* (2013.01); *A61M 25/0113* (2013.01); *A61M 25/0612* (2013.01)

(58) Field of Classification Search
CPC .......... A61M 25/0113; A61M 25/0606; A61M 25/0612; A61M 25/065
See application file for complete search history.

(56) References Cited

U.S. PATENT DOCUMENTS

| 561,059 A | 5/1896 | Mitchell et al. |
|---|---|---|
| 2,705,949 A | 4/1955 | Irving |

(Continued)

FOREIGN PATENT DOCUMENTS

| JP | H03-75748 U | 7/1991 |
|---|---|---|
| JP | H03-75749 U | 7/1991 |

(Continued)

OTHER PUBLICATIONS

International Search Report and Written Opinion issued in International Application No. PCT/JP2011/057010 dated Jun. 28, 2011.

*Primary Examiner* — Shefali D Patel
(74) *Attorney, Agent, or Firm* — Foley & Lardner LLP

(57) ABSTRACT

A catheter assembly includes a hollow catheter; a catheter hub to which the catheter is fixed; an inner needle including a needle tip, the inner needle being detachably disposed inside of the catheter; a needle hub to which the inner needle is fixed; a catheter operation member configured to move the catheter relative to the inner needle; and a support member disposed at the needle hub. The support member includes a support main body portion that is movable between (i) a first position located on a side of the catheter opposite the catheter operation member, at which the catheter is interposed between the support member and the catheter operation member, and the support main body portion contacts and supports the catheter, and (ii) a second position that is a different position from the first position, at which the support main body portion does not contact the catheter.

18 Claims, 16 Drawing Sheets

(56) References Cited

U.S. PATENT DOCUMENTS

| | | |
|---|---|---|
| 2,847,995 A | 8/1958 | Adams |
| 3,225,762 A | 12/1965 | Guttman |
| 3,352,306 A | 11/1967 | Sidney |
| 3,358,684 A | 12/1967 | Gerald |
| 3,463,152 A | 8/1969 | Sorenson |
| 3,509,880 A | 5/1970 | Guttman |
| 3,536,073 A | 10/1970 | Farb |
| 3,584,624 A | 6/1971 | Ciutiis |
| 3,630,195 A | 12/1971 | Santomieri |
| 3,834,380 A | 9/1974 | Boyd |
| 4,108,175 A | 8/1978 | Orton |
| 4,160,450 A | 7/1979 | Doherty |
| 4,194,504 A | 3/1980 | Harms et al. |
| 4,231,367 A | 11/1980 | Rash |
| 4,249,541 A | 2/1981 | Pratt |
| 4,311,137 A | 1/1982 | Gerard |
| 4,327,722 A | 5/1982 | Groshong et al. |
| 4,353,369 A | 10/1982 | Muetterties et al. |
| 4,362,156 A | 12/1982 | Feller, Jr. et al. |
| 4,392,856 A | 7/1983 | Lichtenstein |
| 4,431,426 A | 2/1984 | Groshong et al. |
| 4,439,583 A | 3/1984 | Gould et al. |
| 4,500,312 A | 2/1985 | McFarlane |
| 4,525,157 A | 6/1985 | Vaillancourt |
| 4,529,399 A | 7/1985 | Groshong et al. |
| 4,549,879 A | 10/1985 | Groshong et al. |
| 4,559,046 A | 12/1985 | Groshong et al. |
| 4,588,398 A | 5/1986 | Daugherty et al. |
| 4,627,841 A | 12/1986 | Dorr |
| 4,631,057 A | 12/1986 | Mitchell |
| 4,664,653 A | 5/1987 | Sagstetter et al. |
| 4,664,654 A | 5/1987 | Strauss |
| 4,668,225 A | 5/1987 | Russo et al. |
| 4,671,795 A | 6/1987 | Mulchin |
| 4,671,796 A | 6/1987 | Groshong et al. |
| 4,676,783 A | 6/1987 | Jagger et al. |
| 4,684,369 A | 8/1987 | Wildemeersch |
| 4,690,675 A | 9/1987 | Katz |
| 4,701,166 A | 10/1987 | Groshong et al. |
| 4,702,738 A | 10/1987 | Spencer |
| 4,728,322 A | 3/1988 | Walker et al. |
| 4,747,831 A | 5/1988 | Kulli |
| 4,762,516 A | 8/1988 | Luther et al. |
| 4,770,655 A | 9/1988 | Haber et al. |
| 4,772,264 A | 9/1988 | Cragg |
| 4,772,276 A | 9/1988 | Wiita et al. |
| 4,773,901 A | 9/1988 | Norton |
| 4,778,453 A | 10/1988 | Lopez |
| 4,781,692 A | 11/1988 | Jagger et al. |
| 4,798,597 A | 1/1989 | Vaillancourt |
| 4,826,490 A | 5/1989 | Byrne et al. |
| 4,828,549 A | 5/1989 | Kvalo |
| 4,832,696 A | 5/1989 | Luther et al. |
| 4,834,718 A | 5/1989 | McDonald |
| 4,846,799 A | 7/1989 | Tanaka et al. |
| 4,846,812 A | 7/1989 | Walker et al. |
| 4,863,432 A | 9/1989 | Kvalo |
| 4,887,998 A | 12/1989 | Martin et al. |
| 4,895,564 A | 1/1990 | Farrell |
| 4,898,591 A | 2/1990 | Jang et al. |
| 4,911,691 A | 3/1990 | Aniuk et al. |
| 4,917,671 A | 4/1990 | Chang |
| 4,927,415 A | 5/1990 | Brodsky |
| 4,944,728 A | 7/1990 | Carrell et al. |
| 4,950,252 A | 8/1990 | Luther et al. |
| 4,955,863 A | 9/1990 | Walker et al. |
| 4,976,704 A | 12/1990 | McLees |
| 4,986,814 A | 1/1991 | Burney et al. |
| 4,994,046 A | 2/1991 | Wesson et al. |
| 4,998,919 A | 3/1991 | Schnepp-Pesch et al. |
| 5,002,533 A | 3/1991 | Jullien |
| 5,037,402 A | 8/1991 | Bartman |
| 5,047,018 A | 9/1991 | Gay et al. |
| 5,112,312 A | 5/1992 | Luther |
| 5,120,317 A | 6/1992 | Luther |
| 5,135,502 A | 8/1992 | Koenig, Jr. et al. |
| 5,147,332 A | 9/1992 | Moorehead |
| 5,199,947 A | 4/1993 | Lopez et al. |
| 5,205,829 A | 4/1993 | Lituchy |
| 5,273,540 A | 12/1993 | Luther et al. |
| 5,364,374 A | 11/1994 | Morrison et al. |
| 5,403,283 A | 4/1995 | Luther |
| 5,569,217 A | 10/1996 | Luther |
| 5,873,864 A | 2/1999 | Luther et al. |
| 6,482,180 B2 | 11/2002 | Toyokawa et al. |
| 8,876,773 B2 | 11/2014 | Ishida |
| 9,180,276 B2 | 11/2015 | Ishida |
| 9,265,915 B2 | 2/2016 | Ishida |
| 2003/0220612 A1 | 11/2003 | Hiejima |
| 2008/0082052 A1 | 4/2008 | Schnell et al. |
| 2009/0036836 A1 | 2/2009 | Nystrom et al. |
| 2009/0105651 A1 | 4/2009 | Wada et al. |
| 2013/0023826 A1* | 1/2013 | Ishida ............... A61M 5/158 604/165.02 |

FOREIGN PATENT DOCUMENTS

| | | | |
|---|---|---|---|
| JP | H0375748 U | * | 7/1991 |
| JP | H10-503094 A | | 3/1998 |
| JP | 2002-028246 A | | 1/2002 |
| JP | 2003-339858 A | | 12/2003 |
| JP | 2009-142492 A | | 7/2009 |
| JP | 2009-232916 A | | 10/2009 |
| JP | 2013-529111 A | | 7/2013 |
| WO | WO-2006/090637 A1 | | 8/2006 |
| WO | WO-2007/098355 A1 | | 8/2007 |
| WO | WO-2011/143621 A1 | | 11/2011 |

* cited by examiner

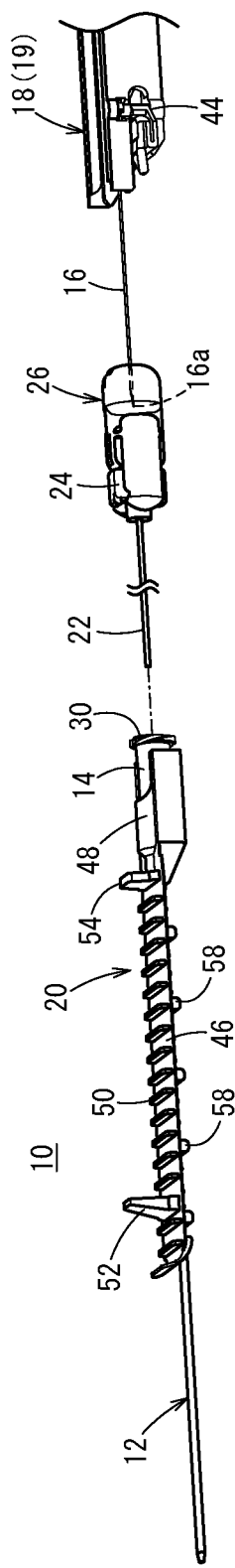
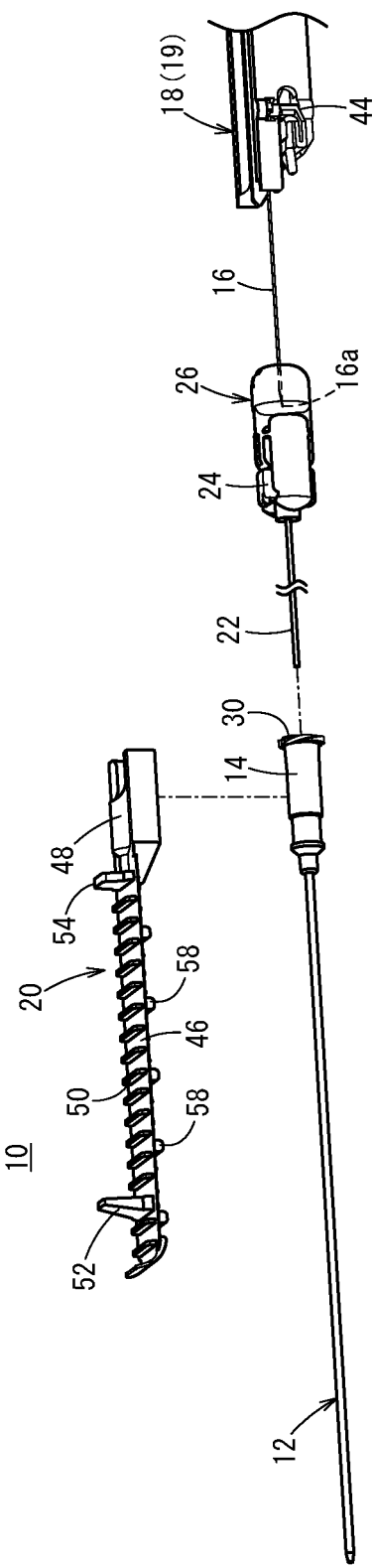
FIG. 4A
FIG. 4B

CATHETER ASSEMBLY

CROSS-REFERENCE TO RELATED APPLICATIONS

This application is a continuation of PCT Application No. PCT/JP2016/063914, filed on May 10, 2016, which claims priority to Japanese Application No. 2015-100357, filed on May 15, 2015. The contents of both of these application are hereby incorporated by reference in their entireties.

BACKGROUND

The present disclosure relates to a catheter assembly adapted to puncture a blood vessel and be indwelled at the time of performing infusion or the like to a patient, for example.

In the related art, a catheter assembly is used at the time of performing infusion or the like to a patient. This kind of the catheter assembly includes a hollow catheter, a catheter hub fixed to a proximal end of the catheter, a hollow inner needle inserted into the catheter and having a sharp needle tip at a distal end, and a needle hub fixed to a proximal end of the inner needle (refer to JP 2013-529111 A).

In the catheter assembly disclosed in JP 2013-529111 A, because the catheter is inserted deep into the patient's body, the long catheter and the inner needle are housed in an axial direction of the inside of the cylindrical-shaped needle hub in a stacking manner. A user such as a doctor or a nurse punctures the patient with the catheter and the inner needle, and performs an advancing operation of a catheter operation member connected to the catheter hub in this puncturing state, thereby making the long catheter advance relative to the inner needle and the needle hub and inserting the same into the body.

SUMMARY

The above-described type of a catheter assembly has a structure in which a distal end side of a needle hub is separated into upper and lower portions at the time inserting a catheter into the inside of a body, and a catheter, a catheter hub, and a catheter operation member are detached from an inner needle and the needle hub after insertion of the catheter. However, in the structure in which the needle hub is thus separated, the catheter and the inner needle extend relative to the needle hub in a non-supported (free) state at the time of inserting the catheter, the catheter is relatively easily warped when reaction force is received from a patient. Depending on the case, a needle tip may retract (slip out) from an inserted portion of the patient and the patient may be punctured again with the needle tip.

Embodiments of the present invention have been made in view of the above-described situation, and are directed to providing a catheter assembly in which a catheter is prevented from being warped by enabling support for the catheter at the time of inserting the catheter, and furthermore, a catheter hub and a catheter operation member can be easily detached from a needle hub.

In order to achieve the above-described objects, a catheter assembly according to one embodiment of the present invention includes: a hollow catheter; a catheter hub adapted to fix and hold the catheter; an inner needle including a needle tip and adapted to be detachably inserted through inside of the catheter; a needle hub configured to fix and hold the inner needle; a catheter operation member capable of moving the catheter relative to the inner needle; and a support member provided at the needle hub. The support member includes a support main body portion that is movable between (i) a first position located on a side of the catheter opposite the catheter operation member, at which the catheter is interposed between the support member and the catheter operation member and the support main body portion contacts and supports the catheter, and (ii) a second position that is a different position from the first position, at which the support main body portion does not contact the catheter.

According to above embodiment, the catheter assembly can support the catheter with the support member located at the first position on an opposite side of the catheter operation member. Therefore, at the time of advancing operation of the catheter operation member, the support member contacts and supports the catheter inside the needle hub and can prevent the catheter from being warped even in the case where the catheter receives reaction force from a patient. Consequently, an extending state of the catheter and the inner needle is maintained, and a user can smoothly insert the catheter into the patient. Furthermore, the support member is displaced from the first position to the second position, thereby making the catheter hub and the catheter operation member advance without interference and achieving easy detachment from the needle hub.

In this case, preferably, the catheter is supported by being interposed between the catheter operation member and the support member in an initial state in which the needle tip projects from a distal end of the catheter.

Thus, because the catheter is supported by being interposed between the catheter operation member and the support member in the initial state, the catheter and the inner needle can be prevented from being warped at the time of puncturing the patient with the catheter and the inner needle. Therefore, the user can perform puncturing with the catheter and the inner needle without any discomfort.

Furthermore, preferably, the support member has the support main body portion inhibited from being moved from the first position in an initial state, and the support main body portion is released from inhibition of movement from the first position along with advancement of the catheter operation member relative to the needle hub.

Thus, because the support member is inhibited from being moved from the first position in the initial state, the catheter can be stably supported. On the other hand, because the support main body portion is released from inhibition of movement at the time of advancement of the catheter operation member, the catheter hub and the catheter operation member can be smoothly exposed from the needle hub.

Moreover, preferably, the catheter operation member includes a holding portion adapted to directly hold the catheter in a detachable manner.

With this structure, because the holding portion directly holds the catheter, warping can be prevented by the catheter operation member at the time of puncture with the catheter and the inner needle and at the time of inserting the catheter. At this point, because the support member can support the catheter on the opposite side of the catheter operation member, the catheter can be prevented from slipping out from the holding portion.

Additionally, preferably, the support member is rotatably attached to the needle hub.

Thus, in the case where the support member is rotatably attached to the needle hub, the support main body portion can be displaced in a short distance between the first position and the second position, and the catheter assembly can be downsized.

Furthermore, preferably, the support member includes an axial rod portion rotatably attached to the needle hub, and the support main body portion projects in a direction orthogonal to an axial direction of the axial rod portion.

With this structure, the support main body portion is rotated around the axial rod portion attached to the needle hub and smoothly displaced between the first position and the second position, and it is possible to easily switch between a catheter supportable state and a detachable state of the catheter hub and the like.

In addition to the above-described components, preferably, the needle hub includes a groove-like rail portion, the axial rod portion includes a groove portion arranged in the rail portion, the catheter operation member includes: a side edge housed in the rail portion and the groove portion in a manner freely slidable and adapted to be guided at the time of relative movement; and a cut-out portion formed by cutting out the side edge at a position same as or near an attachment position to the catheter hub and adapted not to be housed in the rail portion and the groove portion.

With this structure, in the case where the side edge of the catheter operation member exists in the groove portion, the support member becomes unable to be rotated and the catheter supportable state can be continued by making the support main body portion stand by at the first position. On the other hand, in the case where the cut-out portion of the catheter operation member exists in the groove portion, the support member becomes able to be rotated, and the catheter hub and the catheter operation member can be allowed to pass by displacing the support main body portion to the second position.

Furthermore, preferably, the axial rod portion is provided with a cam portion, and the groove portion extends from one end of the cam portion to the other end of the cam portion Thus, because the groove portion is provided across the both ends of the cam portion, a non-rotatable state of the support member by the side edge of the catheter operation member can be more surely maintained. Furthermore, when the cam portion enters the rail portion in a state that the support main body portion is located at the second position, the side edge of the catheter operation member contacts at the time of retraction of the catheter operation member. Consequently, the support main body portion can be displaced from the second position to the first position. This enables the support main body portion to support the catheter again.

Moreover, preferably, the support main body portion includes a projection adapted to contact a proximal end portion of the catheter operation member and displace the support main body portion from the first position to the second position along with advancement of the catheter operation member.

With this structure, the catheter operation member largely rotates the support main body portion by contacting the projection at the time of advancement, and the support main body portion can be surely arranged from the first position to the second position. Therefore, unintended contact between the catheter operation member and the support member can be prevented at the time of retracting operation of the catheter operation member, and the catheter operation member can be made to smoothly retract.

The support member may be a torsion spring including a coil portion formed by winding a wire member and a projecting portion formed as the support main body portion and projecting radially outward from the coil portion.

Thus, because the support member is formed of the torsion spring, the projecting portion can properly support the catheter on the opposite side of the catheter operation member. On the other hand, the projecting portion can easily allow the catheter hub and the catheter operation member to pass by elastic deformation of the coil portion caused by contact of the catheter operation member.

Furthermore, preferably, the support main body portion is elastically deformed in a direction orthogonal to a moving direction of the catheter.

Thus, because the support main body portion is elastically deformed in the direction orthogonal to the moving direction of the catheter, the support main body portion is actively warped even when, for example, the holding portion contacts the same at the time of advancing and retracting operation of the catheter operation member. Therefore, mobility of the catheter operation member can be sufficiently secured.

Additionally, preferably, the support main body portion is inclined downward and outward in a width direction of the needle hub from a portion capable of contacting and supporting the catheter in a state of being arranged at the first position.

Thus, because the support main body portion is inclined downward and outward in the width direction of the needle hub, the catheter detached from the catheter operation member can be received by an inclined upper surface at the time of retraction of the catheter operation member. Therefore, the catheter can be prevented from being deviated in the width direction. Furthermore, the inclined upper surface guides the catheter to an upper portion of the support member and makes the catheter operation member to hold the catheter again.

According to the present invention, in the catheter assembly, the catheter is prevented from being warped by enabling support for the catheter at the time of inserting the catheter and furthermore the catheter hub and the catheter operation member can be easily detached from the needle hub.

BRIEF DESCRIPTION OF THE DRAWINGS

FIG. 4A is a third explanatory diagram illustrating operation of the catheter assembly subsequent to FIG. 3B, and FIG. 4B is a fourth explanatory diagram illustrating operation of the catheter assembly subsequent to FIG. 4A.

DETAILED DESCRIPTION

In the following description, catheter assemblies according to embodiments the present invention will be described in details with reference to the drawings by exemplifying preferable embodiments (first and second embodiments).

In the case of performing transfusion, blood transfusion, and the like to a patient (living body), a catheter assembly 10 according to the present invention is used to construct an introducing portion for medicinal solution and the like by being tapped into the patient's body and indwelled. The catheter assembly 10 may be used as a catheter having a length longer than a peripheral intravenous catheter (such as a central intravenous catheter, a PICC, and a midline intravenous catheter). Note that the catheter assembly 10 may also be formed as a peripheral venous catheter. Furthermore, the catheter assembly 10 is not limited to a venous catheter and may also be formed as an artery catheter such as peripheral artery catheter.

First Embodiment

Figure 1:
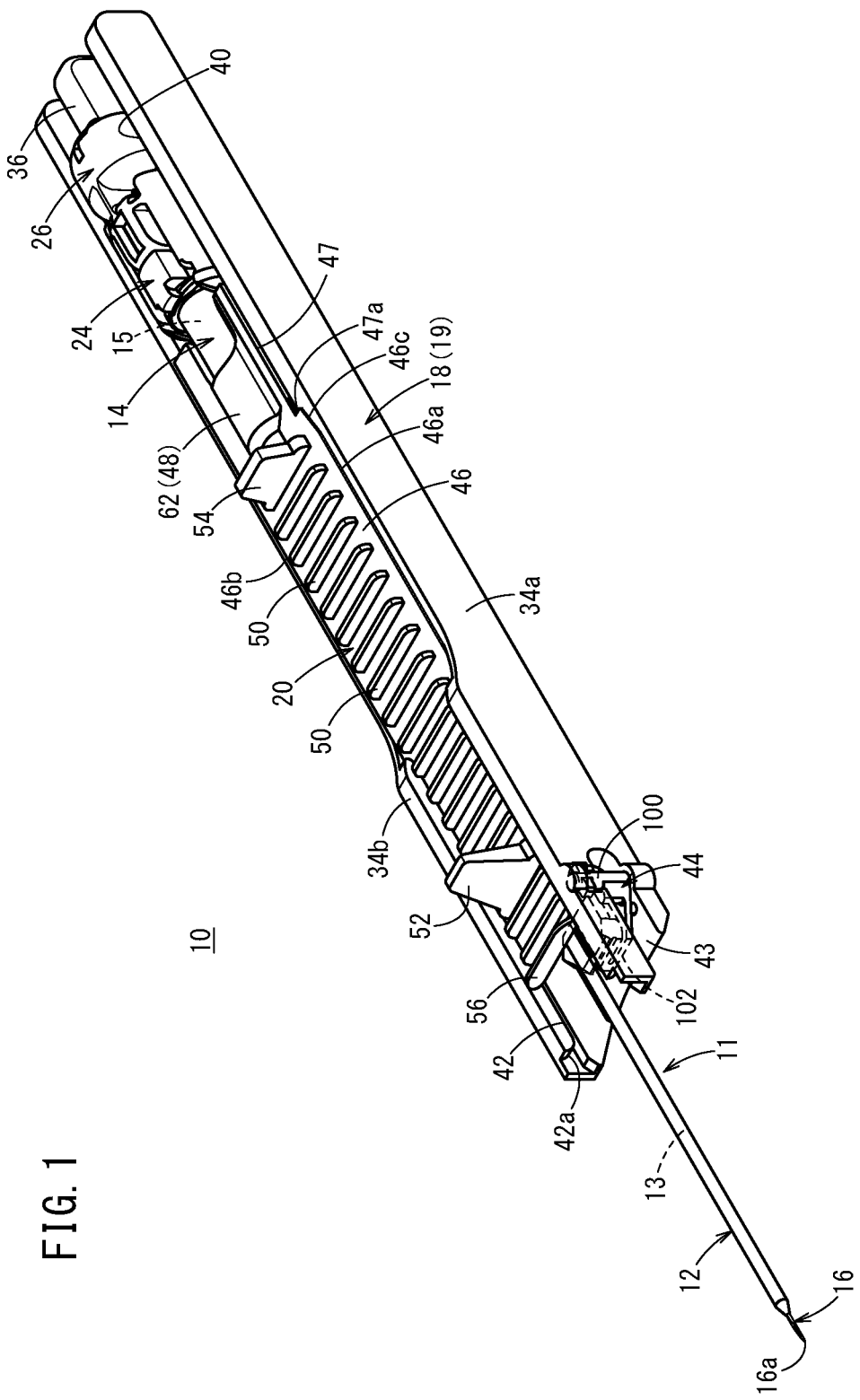
FIG. 1 is a perspective view illustrating an entire structure of a catheter assembly according to a first embodiment of the present invention.
Figure 2:
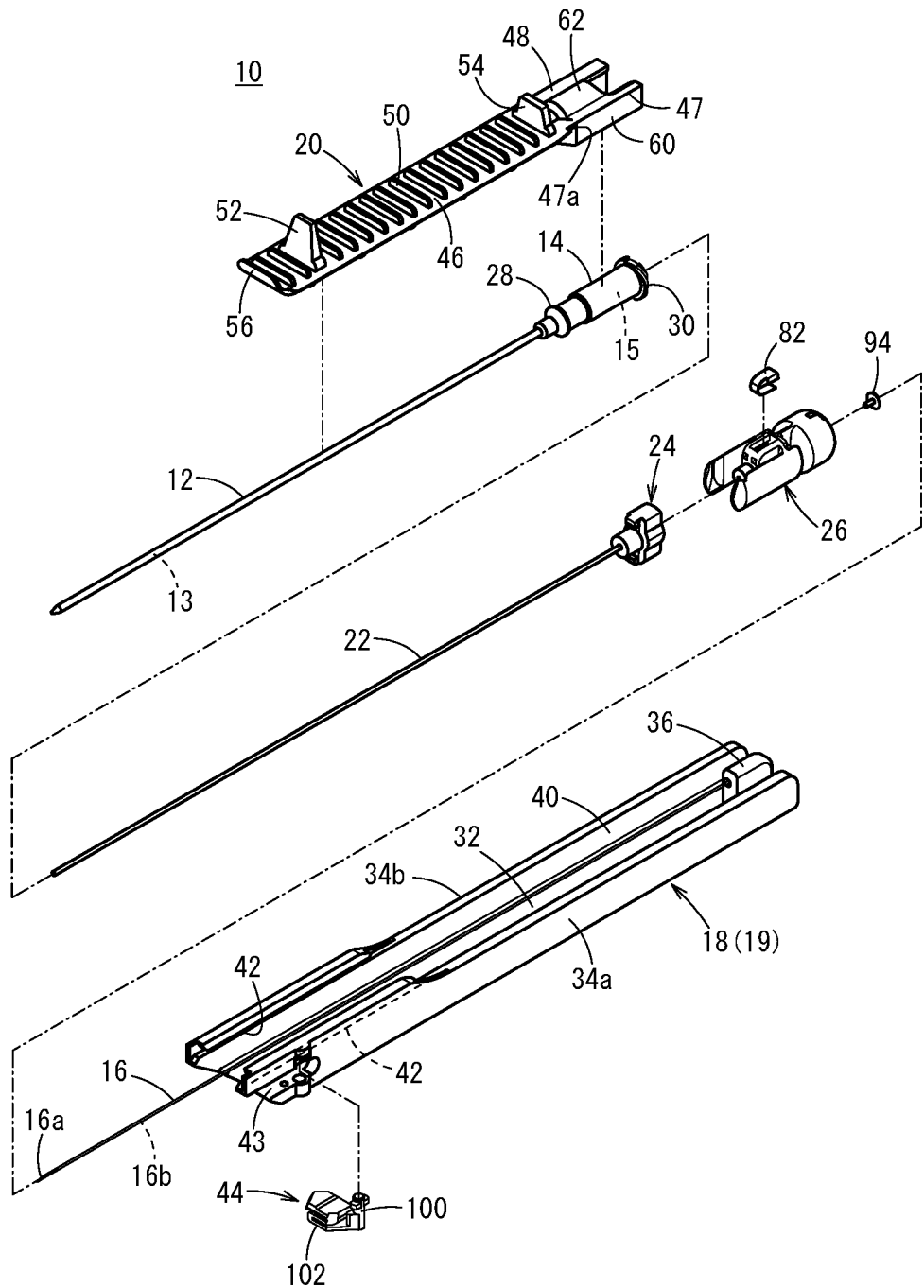
FIG. 2 is an exploded perspective view illustrating the catheter assembly in FIG. 1.

As illustrated in FIGS. 1 and 2, a catheter assembly 10 according to a first embodiment includes a catheter 12, a catheter hub 14 to fixe and hold the catheter 12, a hollow inner needle 16 inserted into the catheter 12, a needle hub 18 to fix and hold the inner needle 16, a catheter operation member 20 attached to an upper side of the catheter hub 14, a tube-like auxiliary member 22 inserted between the catheter 12 and the inner needle 16, an auxiliary member hub 24 to fix and hold the auxiliary member 22, and a needle protection member 26 connected to the catheter hub 14 and a proximal end of the auxiliary member hub 24.

In an initial state before use, the catheter assembly 10 has a multiple tube structure (multiple tube unit 11) in which the catheter 12, auxiliary member 22, and inner needle 16 are stacked sequentially from the outside. The catheter operation member 20 has a structure to directly hold the multiple tube unit 11. Additionally, in the initial state, the catheter assembly 10 houses, inside the needle hub 18, part of the multiple tube unit 11, catheter hub 14, catheter operation member 20, auxiliary member hub 24, and needle protection member 26 by suitably assembling these components.

A user such as a doctor or a nurse grips the needle hub 18 of the catheter assembly 10 in the initial state illustrated in FIG. 1 and punctures a blood vessel (venous or artery) of the patient with a distal end of the multiple tube unit 11. The user performs advancing operation of the catheter operation member 20 relative to the needle hub 18 while keeping the puncturing state, thereby making the catheter 12 advance more to a distal end side (deeper inside the blood vessel) than the inner needle 16.

Figure 3A:
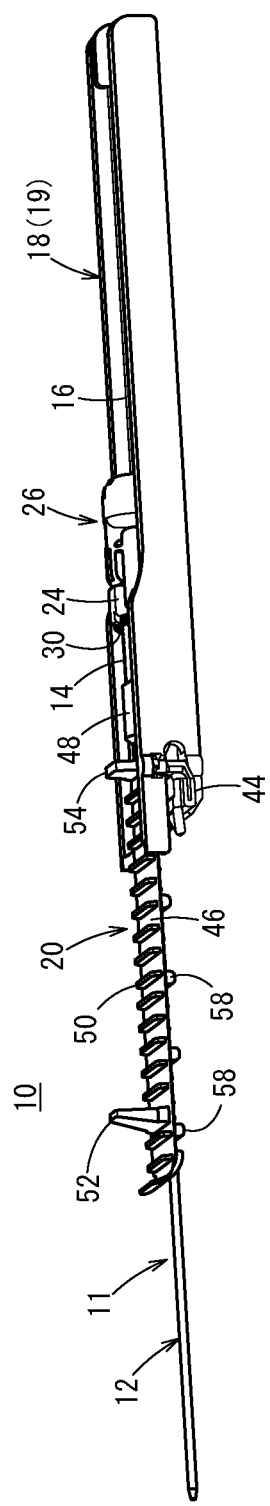
FIG. 3A is a first explanatory diagram illustrating operation at the time of using the catheter assembly.

The catheter assembly 10 also integrally moves the catheter hub 14 connected to the catheter operation member 20, auxiliary member hub 24, and needle protection member 26 as illustrated in FIG. 3A along with advancement of the catheter 12 or retraction of the needle hub 18 relative to the catheter 12. At this point, because the inner needle 16 is fixed to the needle hub 18, the multiple tube unit 11 is changed to have a double-stack structure of the catheter 12 and the auxiliary member 22. Furthermore, the catheter operation member 20 releases the multiple tube unit 11 from being held at the time of performing advancing operation of the catheter 12.

Figure 3B:
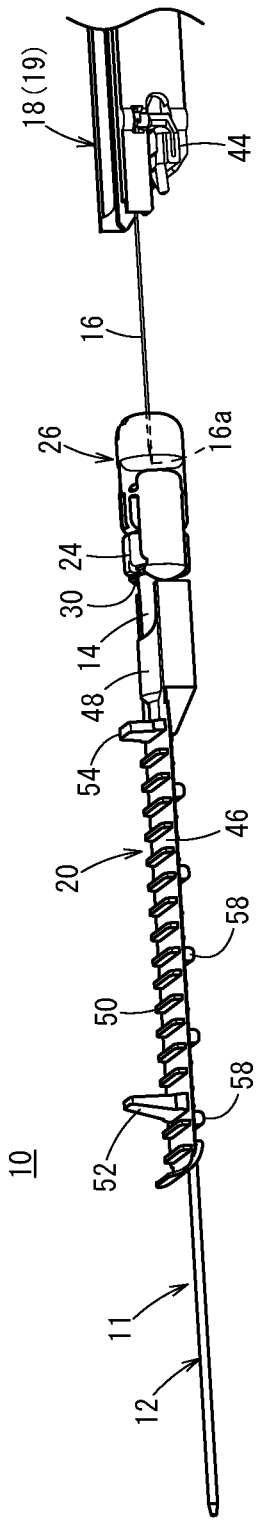
FIG. 3B is a second explanatory diagram illustrating operation of the catheter assembly subsequent to FIG. 3A.

In the case of continuing advancement, a portion up to the needle protection member 26 slips out from the distal end of the needle hub 18, and a needle tip 16a of the inner needle 16 is housed inside the needle protection member 26 as illustrated in FIG. 3B. Then, as illustrated in FIG. 4A, the catheter 12 and the catheter hub 14 can be separated from the auxiliary member hub 24 and the needle protection member 26 which have slipped out from the needle hub 18, and are detached from the auxiliary member 22 along with continuous advancement. Finally, the catheter operation member 20 is detached from the catheter hub 14 as illustrated in FIG. 4B, thereby indwelling the catheter 12 and the catheter hub 14 in the patient. In the following, a structure of the catheter assembly 10 will be specifically described.

As illustrated in FIG. 2, the catheter 12 of the catheter assembly 10 has flexibility, and a cavity 13 is formed inside in a penetrating manner. The cavity 13 is formed to have a diameter capable of housing the inner needle 16 and the auxiliary member 22 and flowing medicinal solution, blood, and the like. A length of the catheter 12 is not particularly limited and can be suitably designed in accordance with usage, conditions, and the like, and for example, the length is set to about 14 to 500 mm, set to about 30 to 400 mm, or set to about 76 to 200 mm.

A constituent material of the catheter 12 is not limited but a soft resin material may be suitable, and for example, fluororesins such as polytetrafluoroethylene (PTFE), ethylene-tetrafluoroethylene copolymer (ETFE), perfluoroalkoxy fluororesin (PFA), olefin resins such as polyethylene and polypropylene, or mixtures thereof, polyurethane, polyesters, polyamides, polyether nylon resins, and mixtures of the olefin resin and ethylene/vinyl acetate copolymer, and the like may be exemplified.

A proximal end of the catheter 12 is fixed to a distal end of the catheter hub 14 by a suitable fixing method (caulking, fusion, bonding, and the like). The catheter hub 14 is exposed on patient's skin with the catheter 12 being inserted into a blood vessel, and indwelled together with the catheter 12 by being pasted with a tape or the like.

The catheter hub 14 is formed in a cylindrical shape tapered in a distal end direction. A constituent material of the catheter hub 14 is not particularly limited, but for example, thermoplastic resins such as polypropylene, polycarbonate, polyamides, polysulfone, polyarylate, and methacrylate-butylene-styrene copolymer may be applied. A transfusion tube connector not illustrated is connected to a proximal end side of the catheter hub 14 after detachment of the inner needle 16.

A hollow portion 15 that is in communication with the cavity 13 of the catheter 12 and allows transfusion solution to flow is provided inside the catheter hub 14. The hollow portion 15 may house a hemostasis valve, a plug, and the like not illustrated adapted to prevent back-flow of blood at the time of puncture with the inner needle 16 and also enable transfusion along with insertion of the transfusion tube connector.

Furthermore, an annular projection 28 which projects radially outward and revolves in a circumferential direction of the catheter hub 14 is formed close to a distal end of an outer peripheral surface of the catheter hub 14. Additionally, same as the annular projection 28, a screw portion 30 that revolves in the circumferential direction of the catheter hub 14 is formed in a projecting manner at a proximal end of the outer peripheral surface of the catheter hub 14.

On the other hand, the inner needle 16 of the catheter assembly 10 is formed as a hollow tube having rigidity capable of puncturing skin of a living body, and arranged in the cavity 13 of the catheter 12 and the hollow portion 15 of the catheter hub 14 in a penetrating manner. The inner needle 16 has an entire length longer than the catheter 12 and is formed to have a diameter gradually becoming larger in the distal end direction from the proximal end portion, and the distal end thereof is provided with a sharp needle tip 16a. In the initial state illustrated in FIG. 1, the multiple tube unit 11 exposes the needle tip 16a from the catheter 12 and the auxiliary member 22. A through-hole 16b is provided inside the inner needle 16 in an axial direction of the inner needle 16. Meanwhile, a groove portion (not illustrated) may also be provided in the axial direction on an outer peripheral surface of the inner needle 16. Additionally, the inner needle 16 may also be a solid needle.

As a constituent material of the inner needle 16, for example, metallic materials such as stainless steel, aluminum or an aluminum alloy, or titanium or a titanium alloy, a hard resin, ceramics, and the like may be exemplified. The inner needle 16 is firmly fixed to the needle hub 18 by a suitable fixing method (fusion, bonding, insert molding, and the like).

Figure 5:
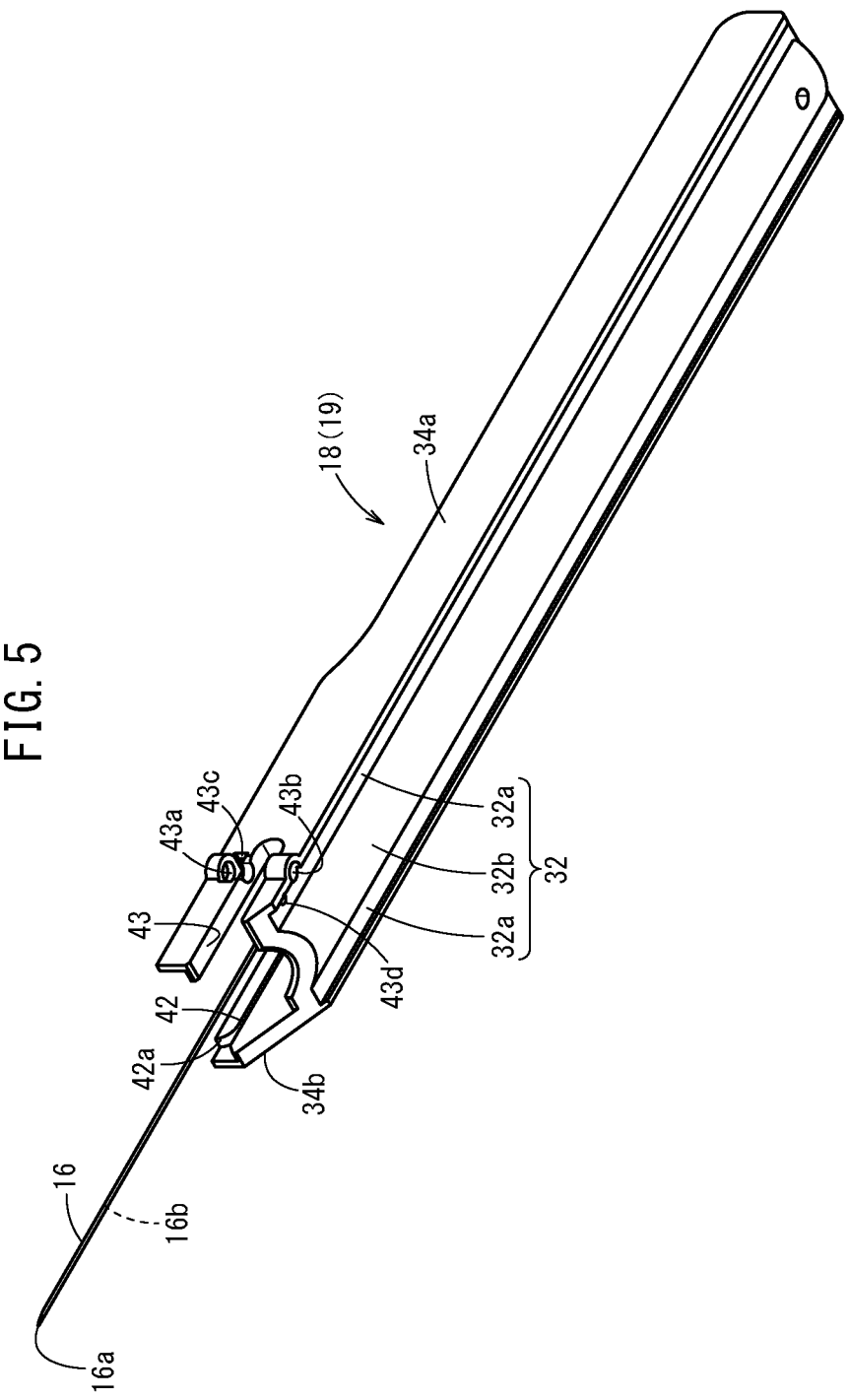
FIG. 5 is a perspective view of an inner needle and a needle hub in FIG. 2 when viewed from a lower side.

As illustrated in FIG. 5, the needle hub 18 is formed as a housing 19 including a lower wall 32, a pair of side walls 34a, 34b projecting upward from a side portions 32a of the lower wall 32. The housing 19 has an elongated cup-like shape extending shorter than an axial length of the inner needle 16. A housing space 40 to house part of the multiple tube unit 11, the catheter hub 14, auxiliary member hub 24, and needle protection member 26 is formed on an inner side surrounded by the lower wall 32 and the pair of side walls 34a, 34b.

A constituent material to form the needle hub 18 is not particularly limited and, for example, may be suitably selected from materials exemplified for the catheter hub 14. Meanwhile, the catheter hub 14 and the needle protection member 26 are exposed on the upper side in order to enable the catheter assembly 10 to rotate the catheter 12 relative to the inner needle 16. Alternatively, the catheter assembly 10 may also have a structure in which the catheter hub 14, needle protection member 26, and the like are covered by forming an upper wall or attaching a lid body to the housing 19.

The lower wall 32 includes: a pair of the side portions 32a formed flat; and a guide groove portion 32b interposed between the pair of the side portions 32a and recessed downward in an arc shape. In the guide groove portion 32b, the catheter hub 14, auxiliary member hub 24, and needle protection member 26 are slidably arranged in a longitudinal direction of the housing 19. On a proximal end side and in a center portion in a width direction of the lower wall 32 (guide groove portion 32b), a needle holding portion 36 projecting upward from an upper surface thereof and adapted to fix the proximal end portion of the inner needle 16 at a predetermined height is integrally formed. Meanwhile, the needle holding portion 36 may also be formed separately from the housing 19 and may be bonded and fixed to the housing 19.

The pair of side walls 34a, 34b extends in parallel in a longitudinal direction together with the lower wall 32 and has a constant vertical width on the proximal end side and an intermediate side, and the vertical width on the distal end side is formed wider relative to the intermediate side. Groove-like rail portions 42 are provided on upper portions on the distal end sides of the respective side walls 34a, 34b. The pair of rail portions 42 linearly extends in the longitudinal direction on inner surfaces of the wide portions of the respective side walls 34a, 34b, and reaches upper surfaces on the intermediate sides. The respective rail portions 42 house side edges 46a, 46b of the catheter operation member 20, and guide advancement and retraction of the catheter operation member 20. A distal end of a groove wall constituting the rail portion 42 is formed to have a curved surface 42a to allow the catheter operation member 20 to be curved.

Furthermore, an arrangement recessed portion 43 to attach a support member 44 is provided on the side wall 34a. The arrangement recessed portion 43 is cut out in the proximal end direction from the distal end of the side wall 34a, and located between the lower wall 32 and the rail portion 42. The lower wall 32 and the side wall 34a at a forming position of the arrangement recessed portion 43 are provided with a pair of bearing holes 43a, 43b to rotatably attach the support member 44. A window 43c in which a cam projecting portion 106 (refer to FIG. 7A) of the support member 44 described later is housed is provided at a position overlapping with the rail portion 42 (between the upper bearing hole 43a and the arrangement recessed portion 43), and an cavity to be arranged with an axial rod portion 100 is formed on a wall between the arrangement recessed portion 43 and the window 43c. Furthermore, a locking recessed portion 43d into which a locking projecting portion 118 is inserted is formed on the lower wall 32 when the support main body portion 102 of the support member 44 is rotated about 90 degrees.

Referring back to FIG. 2, the auxiliary member 22 of the catheter assembly 10 supports the catheter 12 from the inside and has a function to assist insertion of the catheter 12 into a blood vessel. The auxiliary member 22 has an outer diameter smaller than an inner diameter of the catheter 12, and is formed inside a hollow tube having an inner diameter larger than an outer diameter of the inner needle 16. A proximal end portion of the auxiliary member 22 is fixed to and held by the auxiliary member hub 24 by a suitable fixing method (caulking, fusion, bonding, and the like).

The auxiliary member hub 24 has a distal end side thereof assembled to the catheter hub 14 in a freely detachable manner, and the needle protection member 26 is assembled to a proximal end side thereof in a freely detachable manner. The auxiliary member hub 24 connects the catheter hub 14 and the needle protection member 26 respectively in a manner integrally rotatable. Meanwhile, the auxiliary member hub 24 may also integrated to the needle protection member 26 (more specifically, the auxiliary member 22 may also be fixed to the needle protection member 26). Furthermore, the catheter assembly 10 may not necessarily include the auxiliary member 22 and the auxiliary member hub 24. In this case, the needle protection member 26 is directly attached to the proximal end of the catheter hub 14.

In the initial state, the needle protection member 26 has the inner needle 16 arranged in a penetrating manner. Furthermore, the needle tip 16*a* having moved due to detachment of the catheter 12 and the inner needle 16 is housed, and the needle tip 16*a* is prevented from being exposed again. The needle protection member 26 houses a shutter 82 and a slip-out stop member 94 in order to prevent the needle tip 16*a* from being exposed again. The shutter 82 is elastically deformed by contacting the outer peripheral surface of the inner needle 16 in a state that the inner needle 16 is arranged in a penetrating manner, and when the needle tip 16*a* slips out, the shutter 82 is elastically restored and shuts a penetrating route of the inner needle 16. The slip-out stop member 94 includes a hole having a diameter smaller than that of the needle tip 16*a* of the inner needle 16, thereby inhibiting the needle tip 16*a* from slipping out in the proximal end direction.

Figure 6:
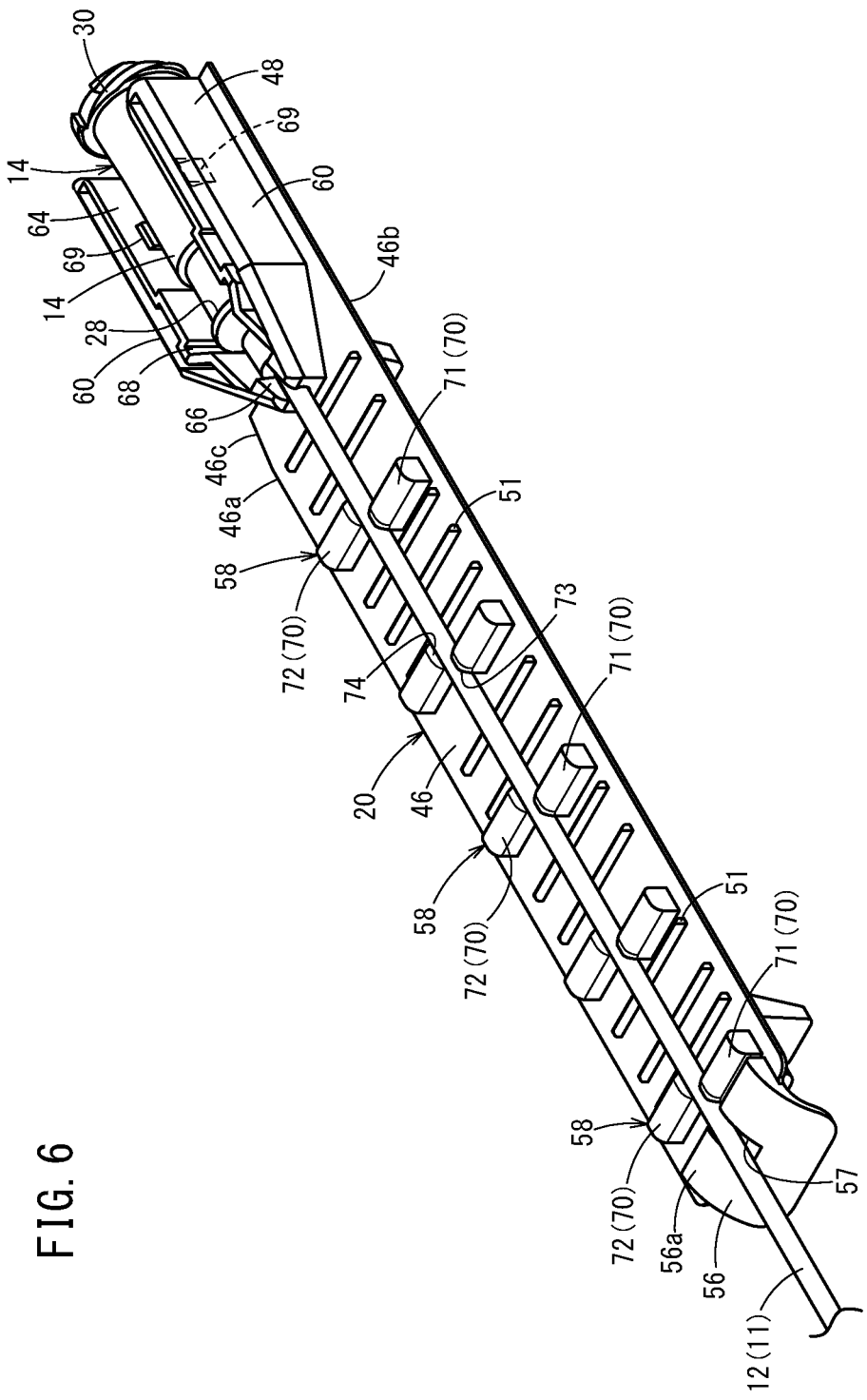
FIG. 6 is a perspective view of a catheter operation member when viewed from an angle different from FIG. 2.

The catheter operation member 20 directly holds the catheter 12 and also is attached to the catheter hub 14, thereby making the catheter 12 and the catheter hub 14 advance and retract relative to the inner needle 16 and the housing 19. As illustrated in FIGS. 2 and 6, the catheter operation member 20 includes an operation plate portion 46 (long portion) extending in the longitudinal direction of the housing 19, and a hub attachment portion 48 integrally formed with a proximal end of the operation plate portion 46 and attached to the catheter hub 14 freely detachably manner.

The operation plate portion 46 is a portion where a user's finger is touched and advancing and retracting operation is performed. In the initial state, a pair of side edges 46*a*, 46*b* of the operation plate portion 46 is arranged at the pair of rail portions 42 and upper surfaces of the pair of side walls 34*a*, 34*b* on the proximal end sides of the rail portions 42. The operation plate portion 46 is formed thin enough to have flexibility capable of being curved in a direction orthogonal to a surface direction of the operation plate portion 46, more specifically, in a direction separating away from the inner needle 16. A constituent material of the operation plate portion 46 (catheter operation member 20) is not particularly limited and, for example, may be suitably selected from the materials exemplified for the catheter hub 14.

As illustrated in FIG. 1, the operation plate portion 46 is formed a substantially rectangular shape in a plan view, and a cut-out portion 47 is provided on a proximal end side of a side edge 46*a* (setting place side of the support member 44). The cut-out portion 47 forms a level difference 47*a* at a boundary between a forming position thereof and the operation plate portion 46 by cutting off the operation plate portion 46 toward the inside in a width direction. Furthermore, an inclined edge 46*c* gradually inclined toward the inside in the width direction in the proximal end direction is formed at the side edge 46*a* located more on the distal end side than the level difference 47*a*.

Additionally, as illustrated in FIGS. 2 and 6, an upper side rib 50 and tabs 52, 54 are provided on an upper surface of the operation plate portion 46, a distal end camber portion 56 is provided at a distal end of the operation plate portion 46, and a holding portion 58 and a lower side rib 51 are provided on a lower surface of the operation plate portion 46.

A plurality of upper side ribs 50 and a plurality of lower side ribs 51 are provided in a longitudinal direction of the operation plate portion 46. These upper and lower side ribs 50, 51 project upward and downward respectively and linearly extend in a width direction of the operation plate portion 46, thereby enhancing strength in the width direction of the operation plate portion 46. With this structure, the operation plate portion 46 is prevented from being bent, warped, or the like inside the housing 19 even when external force is applied from the outside, and advancing and retracting is smoothly performed along the upper surfaces of the pair of side walls 34*a*, 34*b* and the rail portions 42.

The tabs 52, 54 are portions provided assuming that the user's finger directly touches the same, and the tabs project higher than the upper side rib 50. The number of tabs 52, 54 to be provided is not limited to two illustrated in FIG. 2, and one tab or three or more tabs may be provided.

As illustrated in FIG. 6, the distal end camber portion 56 includes a thick portion 56*a* projecting to the lower surface side of the operation plate portion 46, and becomes gradually thinner from the thick portion 56*a* in the distal end direction while being curved upward. An insertion groove 57 through which the catheter 12 is made to pass in a non-contacting manner or with little friction is formed at a center portion in a width direction of the thick portion 56*a*. With advancement of the catheter operation member 20, a cambered lower surface side of the distal end camber portion 56 contacts the patient or is gripped by the user, thereby guiding the operation plate portion 46 to be directed obliquely upward.

On the other hand, a plurality of holding portions 58 of the catheter operation member 20 is provided in the longitudinal direction of the operation plate portion 46 (five holding portions in FIG. 6). The holding portions 58 are arranged at equal intervals in the longitudinal direction of the operation plate portion 46, and hold the catheter 12 at the respective places by contacting the outer peripheral surface thereof. Meanwhile, the catheter operation member 20 may also have a structure in which one holding portion 58 is provided at one predetermined place to hold the catheter 12.

The plurality of holding portions 58 each includes a pair of projecting pieces 70 (projecting portions) projecting downward from the lower surface of the operation plate portion 46. The pair of projecting pieces 70 is symmetrically formed each other interposing an intermediate portion in the width direction of the operation plate portion 46 (in the following, a projecting piece 70 located on a near side in FIG. 6 will be also referred to as a first projecting piece 71 and a projecting piece 70 located on a far side in FIG. 6 will be also referred to as a second projecting piece 72).

The first and second projecting pieces 71, 72 are formed in a rectangular shape that is wide in the width direction of the operation plate portion 46. An interval of respective inner edges of the first projecting piece 71 and the second projecting piece 72 is set slightly wider than the outer diameter of the catheter 12. Nail portions 73, 74 slightly projecting to an inner side in the width direction are formed on lower portion sides of the respective inner edges. An interval of respective projecting ends of the pair of the nail portions 73, 74 is set slightly narrower than the outer diameter of the catheter 12 by coming close to each other.

When the catheter 12 is assembled to the catheter operation member 20, the catheter 12 passes the pair of nail portion 73, 74 and is easily nipped between the first and second projecting pieces 71, 72. Meanwhile, "nipped" in the present specification means a state that the holding portions 58 contact and hold the catheter 12 with weak engagement force. Needless to mention, the structure of the holding portion 58 is not limited to the above-described pair of the projecting pieces 70, and various kinds of structures to hold the catheter 12 are applicable.

The first and second projecting pieces 71, 72 are formed in a square shape having round corners at protruding ends (lower ends) in side sectional view. The round corners of the first and second projecting pieces 71, 72 allow the support member 44 located on the lower side to easily climb over the first and second projecting pieces 71, 72 (improves slidability) when the catheter operation member 20 advances and retracts.

Moreover, the first and second projecting pieces 71, 72 are formed in a projecting manner such that phases (forming positions) are mutually deviated in the longitudinal direction of the operation plate portion 46. In other words, the first projecting piece 71 and the second projecting piece 72 hold the catheter 12 with weak engagement force by not clamping the catheter 12 on the same axis. Therefore, when the operation plate portion 46 is curved, the catheter operation member 20 displaces and detaches hooked portions of the catheter 12 in the order of the first projecting piece 71 and the second projecting piece 72.

On the other hand, the hub attachment portion 48 of the catheter operation member 20 is formed in a box shape by a pair of side plates 60 projecting downward from the operation plate portion 46 and a semi-cylindrical upper plate 62 slightly projecting upward from the operation plate portion 46. In the case of viewing the hub attachment portion 48 from the lower direction, a proximal end side and an intermediate side of the pair of the side plates 60 extend in parallel and a distal end side continuous to the intermediate side is inclined inward in the distal end direction.

The catheter hub 14 is rotatably housed inside the pair of side plates 60 and the upper plate 62 while an attachment chamber 64 to inhibit axial movement of the catheter hub 14 relative to the hub attachment portion 48 is provided. The attachment chamber 64 is open to the outside at the lower portion and the proximal end of the hub attachment portion 48.

An inner surface of the attachment chamber 64 is formed with: a locking groove 66 formed by overlaying a trapezoid hole on a round hole; a groove portion 68 adapted to arrange the pair of side plates 60 and the upper plate 62 extending in a U-shape; and a pair of projections 69 projecting inside the hub attachment portion 48. The locking groove 66 allows the catheter 12 to pass through the trapezoid hole having a wide lower side and a narrow upper side and then be arranged in the round hole, and appropriately locks the catheter 12 by hooking the catheter at a boundary portion between the trapezoid hole and the round hole. The groove portion 68 rotatably houses the annular projection 28 of the catheter hub 14 in a manner inhibiting movement thereof in the distal end and proximal end directions. Furthermore, the pair of projections 69 hooks the outer peripheral surface on the proximal end side of the catheter hub 14 with light engagement force.

Furthermore, as illustrated in FIG. 2, because the catheter assembly 10 supports the lower side of the catheter 12 held by the catheter operation member 20, the support member 44 is provided at the distal end side of the housing 19. The support member 44 includes the cylindrical axial rod portion 100 and the support main body portion 102 projecting in a lateral direction from the axial rod portion 100 (direction orthogonal to an axial center of the axial rod portion 100).

Figure 7A:
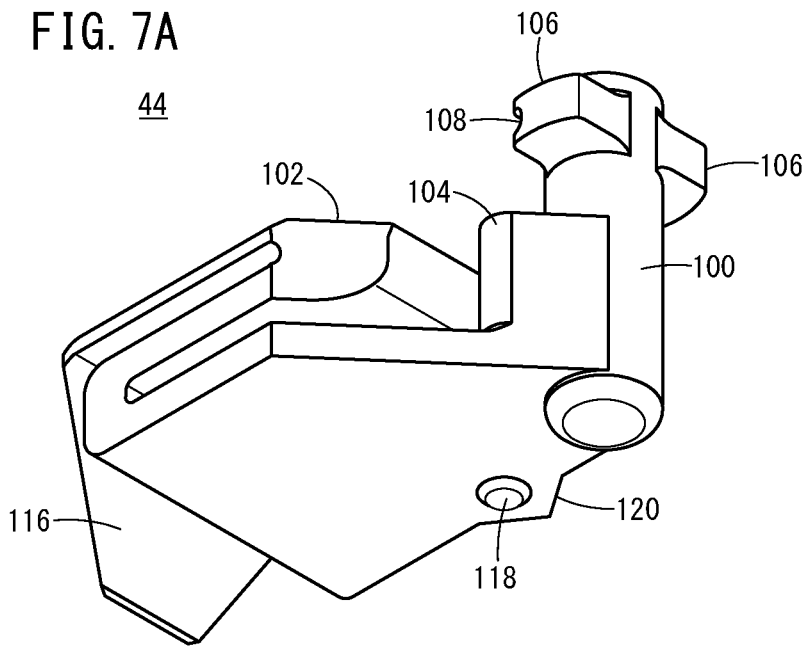
FIG. 7A is a perspective view of a support member when viewed from a lower side.
Figure 7B:
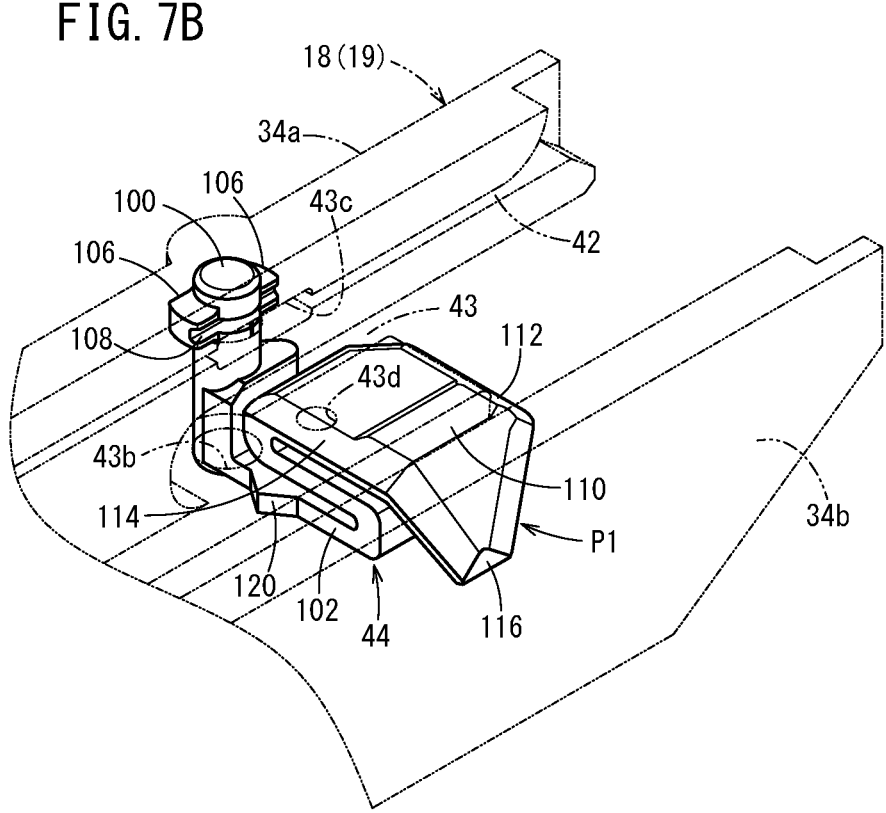
FIG. 7B is a perspective view of the support member when viewed from an obliquely upper side.

As illustrated in FIGS. 2, 7A and 7B, the axial rod portion 100 extends short in upper and lower directions, and an upper end portion and a lower end portion are inserted in to the pair of upper and lower bearing holes 43a, 43b of the arrangement recessed portion 43 respectively. The support member 44 is assembled to the housing 19 in a manner rotatable around the axial rod portion 100 as a base point.

A connection reinforcing portion 104 corresponding to a vertical length of the arrangement recessed portion 43 is formed in a bulging manner on the lower side of the axial rod portion 100 in a state that the support member 44 is assembled to the housing 19. The support main body portion 102 is connected to the connection reinforcing portion 104. Furthermore, a pair of the cam projecting portions 106 (cam portions) functioning as a cam portion adapted to rotatably operate the support member 44 is integrally formed on an upper side of the axial rod portion 100. The pair of cam projecting portions 106 is provided at a predetermined position (position housed in the window 43c in a state of being assembled to the housing 19), and projects mutually in opposite directions to the same extent, interposing the axial rod portion 100.

Furthermore, the support member 44 includes an operation member groove portion 108 at a position facing the axial rod portion 100 and the support main body portion 102 of the pair of cam projecting portions 106. The operation member groove portion 108 linearly extends from a most distal end of the cam projecting portion 106 on the distal end side to a most proximal end of the cam projecting portion 106 on the proximal end side in the initial state. The operation member groove portion 108 is arranged at a position corresponding to the rail portion 42, and houses the side edge 46a of the catheter operation member 20 in a slidable manner together with the rail portion 42.

Figure 10A:
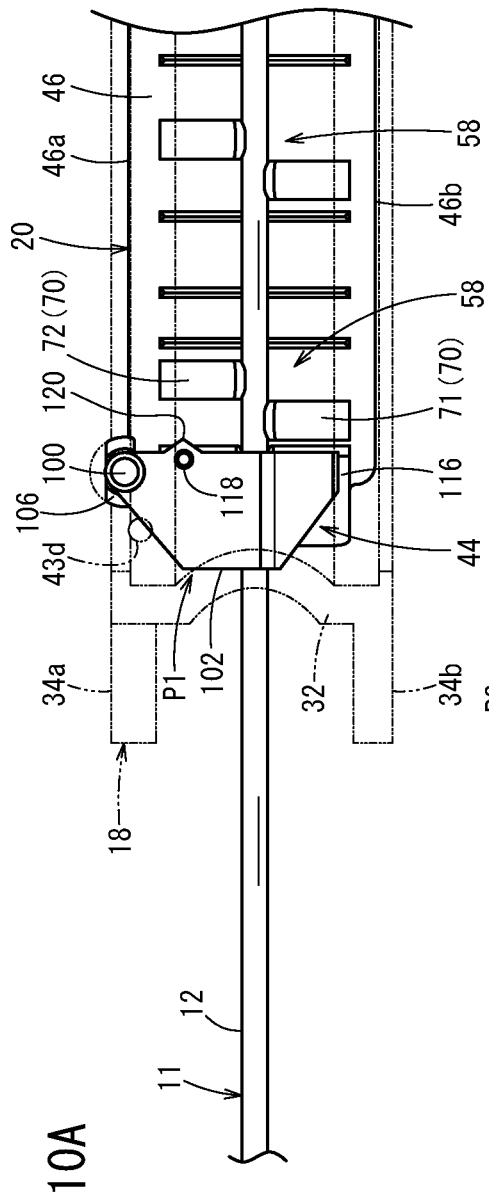
FIG. 10A is a plan view illustrating a state in which a support main body portion is positioned at a first position when viewed from a lower side.
Figure 10B:
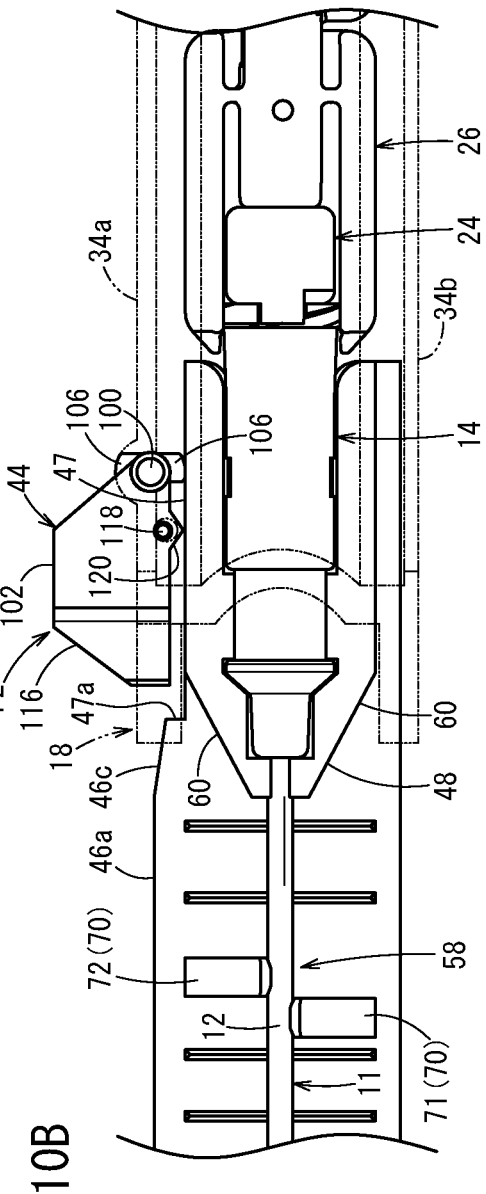
FIG. 10B is a plan view illustrating a state in which the support main body portion is positioned at a second position when viewed from a lower side.

On the other hand, the support main body portion 102 of the support member 44 is a portion to be moved by rotation around the axial rod portion 100 as the rotation point in a state of being assembled to the housing 19. More specifically, the support main body portion 102 is displaced to a first position P1 located inside the housing space 40 and capable of contacting and supporting the catheter 12 (refer to FIGS. 7B and 10A) and a second position P2 located outside the housing 19 and in the arrangement recessed portion 43 different from the first position P1, and not contacting the catheter 12 (refer to FIG. 10B). An angle between the first position P1 and the second position P2 around the axial center of the axial rod portion 100 is preferably 90 degrees or more such that the catheter hub 14, auxiliary member hub 24, and needle protection member 26 can easily slip out. According to the present embodiment, the angle is set to 90 degrees such that the cam projecting portion 106 is located inside the rail portion 42 at the second position P2.

The support main body portion 102 is formed in an S shape having a size almost same as the vertical width of the arrangement recessed portion 43 in a front view, and has spring force capable of being elastically deformed in the vertical direction. A raised portion 110 slightly rising upward is formed on an upper surface of the support main body portion 102. The raised portion 110 is the first position P1 of the support main body portion 102 and can contact the catheter 12 (multiple tube unit 11) held by the catheter operation member 20. Meanwhile, in the present embodiment, the support main body portion 102 faces the catheter 12 in a non-contacting manner in a state of being located in the first position P1, and is adapted to contact and support the same when pressed by the user. However, not limited thereto, the support main body portion 102 may be adapted to contact and support the catheter 12 when located in the first position P1.

Furthermore, a distal end inclined surface 112 inclined downward and in the distal end direction is formed on an upper distal end side of the support main body portion 102, and a proximal end inclined surface 114 inclined downward and in the proximal end direction is formed on an upper proximal end side of the support main body portion 102. Additionally, awing 116 projecting and inclined downward and outward in a width direction separating from the axial rod portion 100 is integrally formed at an end portion continued to the raised portion 110 of the support main body portion 102.

The locking projecting portion 118 is formed downward in a projecting manner on a lower surface of the support main body portion 102. The locking projecting portion 118 is inserted into the locking recessed portion 43d of the housing 19 at the second position P2 of the support main body portion 102. Furthermore, a contacting projection 120 projecting the proximal end direction is provided at a proximal end on a lower portion side of the support main body portion 102. The contacting projection 120 contacts the side plates 60 (hub attachment portion 48) at the time of advancement of the catheter operation member 20, and induces the support main body portion 102 to be displaced to the second position P2 distant from the first position P1 by 90 degrees.

A constituent material of the support member 44 is not particularly limited and, for example, may be suitably selected from the materials exemplified for the catheter hub 14. Meanwhile, the support member 44 may be provided not only as a separate body from the housing 19 but also formed integrally with the housing 19. Furthermore, the support member 44 may not only provided at the side wall 34a of the housing 19 but also provided at the side wall 34b, and a pair thereof may be provided at both of the side walls 34a, 34b. Additionally, a rotational direction of the support main body portion 102 is not limited to the plane direction of the housing 19 but in a side surface direction including upward and downward.

The catheter assembly 10 according to the present embodiment has the basic structure as described above, and functions and effects thereof will be described below.

As described above, the catheter assembly 10 is used to construct an introducing portion for transfusion to a patient. In the initial state illustrated in FIG. 1, the catheter hub 14, auxiliary member hub 24, and needle protection member 26 are connected, and the catheter hub 14 is housed in the attachment chamber 64 of the catheter operation member 20 (hub attachment portion 48) and integrally housed in the housing space 40 of the housing 19.

Figure 8:
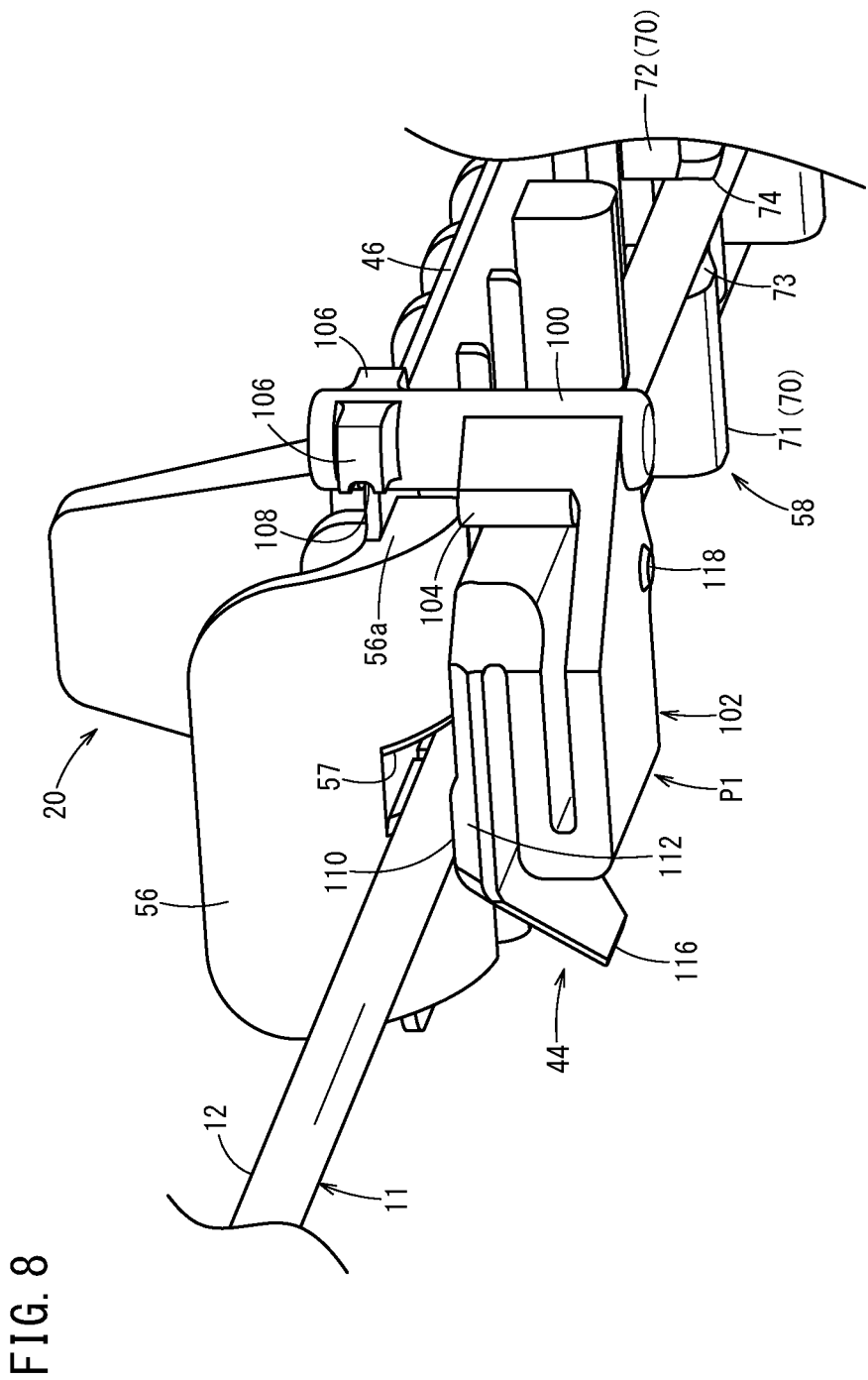
FIG. 8 is a perspective view illustrating an enlarged supporting state of the catheter by the catheter operation member and the support member.

Furthermore, in the initial state, the support main body portion 102 of the support member 44 assembled to the distal end portion of the housing 19 stands by at the first position P1, and faces the multiple tube unit 11 held by the plurality of holding portions 58 of the catheter operation member 20 as illustrated in FIG. 8. Each of the holding portions 58 nips the outer peripheral surface of the catheter 12 with weak engagement force in each place in the axial direction, and the catheter 12 is firmly held as the entire catheter operation member 20.

At the time of using the catheter assembly 10, the user grips and operates the housing 19, and punctures a patient with the multiple tube unit 11. At the time of puncture, the holding portions 58 hold the catheter 12, thereby preventing the multiple tube unit 11 from being warped inside the housing 19 even when resistance force is received along with puncture. Furthermore, when the distal end side of the catheter operation member 20 is pressed downward by the user's finger at the time of puncture, the multiple tube unit 11 is contacted and supported by the support member 44 standing by at the first position P1. Therefore, the multiple tube unit 11 is more prevented from being warped by being fixed between the catheter operation member 20 (insertion groove 57 of the distal end camber portion 56) and the support member 44 (raised portion 110).

As a result, the extending state of the multiple tube unit 11 from the distal end of the housing 19 is properly maintained, and the user can puncture the patient with the multiple tube unit 11 without any discomfort. Furthermore, the catheter assembly 10 can be formed thinner by reducing strength of the inner needle 16, and burden on the patient can be reduced.

As illustrated in FIG. 3A, in a puncture state with the multiple tube unit 11, the user makes the catheter 12 advance relative to the inner needle 16 and inserts the same into a blood vessel. At this point, the user puts a finger on the upper side rib 50 or the tabs 52, 54 of the catheter operation member 20 and makes the catheter operation member 20 advance in the distal end direction relative to the housing 19 (relative movement). In advancing operation of the catheter operation member 20, the multiple tube unit 11 is kept being held by the holding portions 58, and the catheter 12 smoothly advances.

Figure 9A:
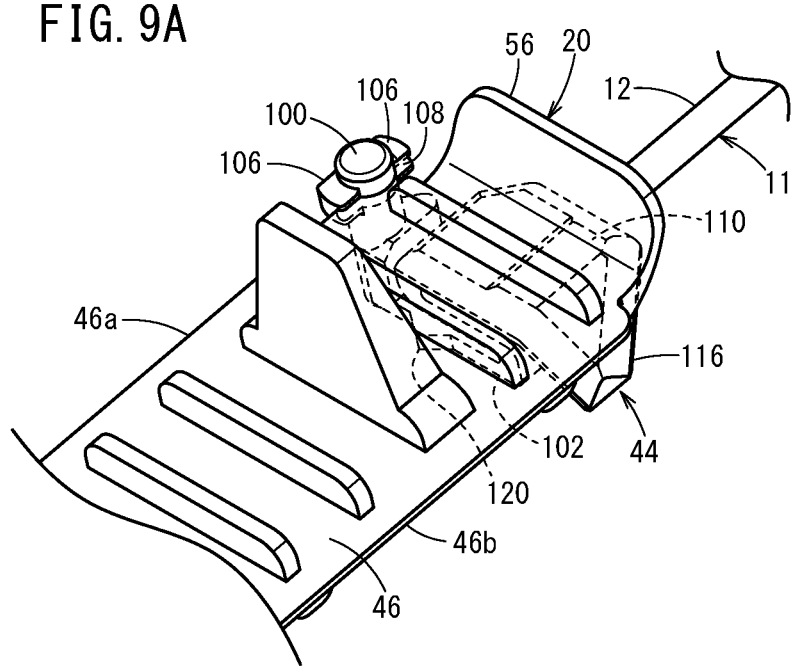
FIG. 9A is a perspective view illustrating a state in which a side edge of the catheter operation member is positioned in an operation member groove of the support member.

At the time of advancing operation, because the side edge 46a of the operation plate portion 46 exists in the operation member groove portion 108 of the support member 44 as illustrated in FIG. 9A, the support member 44 is prevented from being rotated, and the support main body portion 102 continues standing by at the first position P1. Therefore, the support member 44 keeps the state capable of supporting the lower side of the multiple tube unit 11, and the multiple tube unit 11 is prevented from slipping out from the holding portions 58 even in the case where the catheter 12 receives reaction force from the skin and the like at the time of inserting the catheter 12. Therefore, for example, the needle tip 16a of the inner needle 16 is prevented from retracting and slipping out from the skin by being warped, and inconvenience such as puncturing the skin again with the inner needle 16 can be avoided.

Furthermore, because the support main body portion 102 has elastic force in the vertical direction and includes the proximal end inclined surface 114, the support main body portion 102 is suitably and elastically deformed to allow the holding portion 58 to pass when contacted by the holding portion 58 (pair of projecting pieces 70) at the time of advancement. Consequently, the catheter operation member 20 makes the catheter 12 smoothly advance.

When the distal end camber portion 56 contacts the patient's skin along with advancement in the distal end direction or when the user grips the distal end camber portion 56 or the like, the operation plate portion 46 of the catheter operation member 20 is curved in a manner separating away from the axial direction of the multiple tube unit 11. The operation plate portion 46 is curved from the distal end side of the operation plate portion 46, and the holding portions 58 aligned in the longitudinal direction sequentially detach the multiple tube unit 11 from the distal end side against respective engagement force. Even in the case where holding by the holding portion 58 on the distal end side is released due to curving of the operation plate portion 46, the holding portion 58 on the proximal end side where linearity is kept inside the housing 19 can continue holding the multiple tube unit 11. Furthermore, the support main body portion 102 of the support member 44 keeps standing by at the first position P1 and continues supporting the multiple tube unit 11 together with the holding portions 58 holding the catheter 12 on the proximal end side.

Here, in the case where the user cannot insert the catheter 12 smoothly, the user can once perform retracting operation of the catheter operation member 20 and may make the catheter 12 retract relative to the inner needle 16 and the housing 19. At the time of retraction, the operation plate portion 46 is housed again in the rail portions 42 of the housing 19 and the curved state is changed to the linear state (non-curved state). Furthermore, due to retraction of the catheter operation member 20, the wing 116 and the raised portion 110 lift the catheter 12 toward the holding portions 58, and make the plurality of holding portions 58 (pair of projecting pieces 70) nip the catheter 12 again.

Figure 9B:
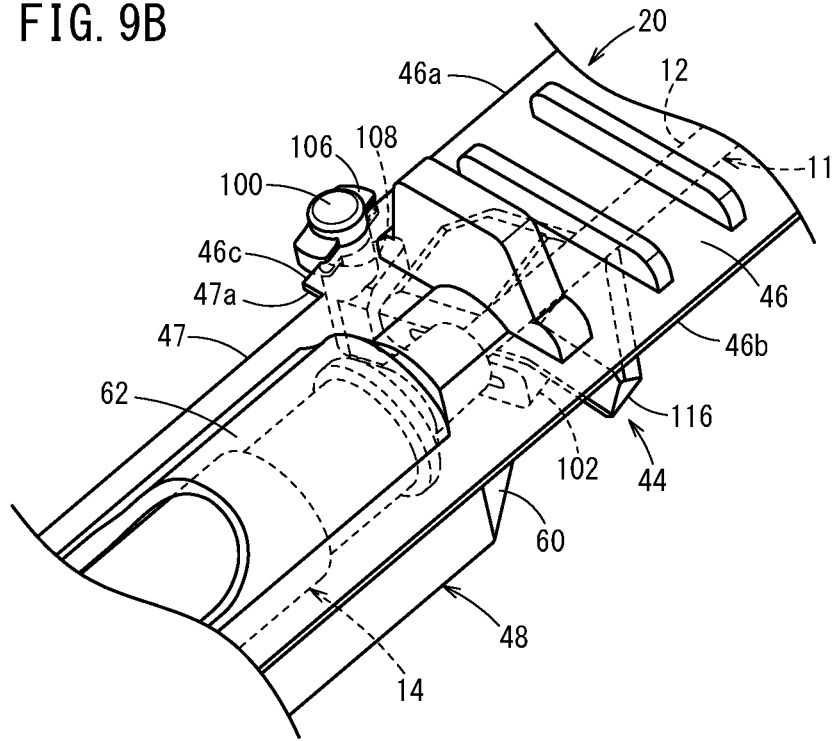
FIG. 9B is a perspective view illustrating a state in which an inclined edge of the catheter operation member is positioned in the operation member groove portion of the support member.

When the catheter operation member 20 advances to some extent, a state in which the side edge 46a illustrated in FIG. 9A is located in the operation member groove portion 108 is shifted to a state in which the inclined edge 46c of the operation plate portion 46 illustrated in FIG. 9B is located in the operation member groove portion 108. At the same time, the side plates 60 of the hub attachment portion 48 contact the contacting projection 120 of the support main body portion 102, thereby starting rotation of the support main body portion 102 from the first position P1.

When the level difference 47a of the operation plate portion 46 passes the cam projecting portion 106 on the distal end side of the support member 44, the cam projecting portion 106 comes to be located at the cut-out portion 47 and the support member 44 becomes rotatable. The contacting projection 120 of the support main body portion 102 rotates the support main body portion 102 with the sufficient rotation angle (90 degrees) by contact of the catheter operation member 20. As a result, the support main body portion 102 is displaced from the first position P1 illustrated in FIG. 10A to the second position P2 illustrated in FIG. 10B, and largely open a distal end side of the housing space 40. Consequently, the catheter hub 14, auxiliary member hub 24, and needle protection member 26 can pass in the distal end direction and can easily slip out from the housing 19.

In the state that the support main body portion 102 is located at the second position P2, the locking projecting portion 118 is inserted into the locking recessed portion 43d, thereby making the support main body portion 102 stand by at the second position P2. Further, in this state, one of the cam projecting portions 106 is located inside the rail portion 42. Therefore, when the user perform retracting operation of the catheter operation member 20, the support member 44 is rotated by contact of the level difference 47a and the cam projecting portion 106, and the support main body portion 102 is returned to the first position P1 from the second position P2 again. When the support main body portion 102 is rotated, the wing 116 extends obliquely downward. Therefore, the catheter 12 is guided to an upper portion of the support main body portion 102 while the catheter 12 is prevented from being deviated in the lateral direction. Therefore, the support member 44 can make the holding portions 58 nip the catheter 12 again along with retraction of the catheter operation member 20.

With advancement of the catheter operation member 20 (or with retraction of the inner needle 16 and the housing 19), the catheter hub 14 attached to the hub attachment portion 48 and the needle protection member 26 attached to the catheter hub 14 also advance. Furthermore, when the catheter hub 14 and the needle protection member 26 slip out from the housing 19 and advance to some extent, the needle tip 16a of the inner needle 16 is housed inside the needle protection member 26. The needle protection member 26 inhibits the needle tip 16a from slipping out by the slip-out stop member 94, and also prevents the needle tip 16a from being exposed again by opening, in front of the needle tip 16a, the shutter 82 that has been closed by the outer peripheral surface of the inner needle 16 inside the needle protection member 26.

Furthermore, after the catheter hub 14 is detached from the housing 19, engagement between the locking groove 66, pair of projections 69 of the hub attachment portion 48, and catheter hub 14 can be easily released. Therefore, the user separates the catheter operation member 20 from the catheter 12 and the catheter hub 14 at suitable timing, and the catheter 12 and the catheter hub 14 are properly indwelled in the patient.

As described above, the catheter assembly 10 according to the present embodiment can support the catheter 12 with the support member 44 located at the first position P1 on an opposite side of the catheter operation member 20. Therefore, at the time of advancing operation of the catheter operation member 20, the support member 44 contacts and supports the catheter 12 inside the housing 19 and can prevent the same from being warped even in the case where the catheter 12 receives reaction force from a patient. Consequently, the extending state of the multiple tube unit 11 is properly maintained, and the user can smoothly insert the catheter 12 into the patient. Furthermore, the support member 44 is displaced from the first position P1 to the second position P2, thereby making the catheter hub 14 and the catheter operation member 20 advance without interference and enabling easy detachment from the inner needle 16 and the housing 19.

In the catheter assembly 10, the catheter 12 is supported by being interposed between the catheter operation member 20 and the support member 44 in the initial state. Consequently, the multiple tube unit 11 can be prevented from being warped at the time of puncturing the patient with the multiple tube unit 11. Therefore, the user can perform puncture with the multiple tube unit 11 without any discomfort. Furthermore, because the support main body portion 102 is inhibited from being moved from the first position P1 in the initial state, the catheter 12 can be stably supported. On the other hand, because the support main body portion 102 is released from inhibition of movement at the time of advancement of the catheter operation member 20, the catheter hub 14 and the catheter operation member 20 can be smoothly exposed from the housing 19. Furthermore, because the holding portions 58 directly hold the catheter 12, warping can be prevented by the catheter operation member 20 at the time of puncture with the multiple tube unit 11 and the catheter 12 and at the time of inserting the catheter 12. At this point, because the support member 44 can support the catheter 12 on the opposite side of the catheter operation member 20, the catheter 12 can be prevented from slipping out from the holding portion 58.

In this case, when the support member 44 is rotatably attached to the housing 19, the support main body portion 102 can be displaced in a short distance between the first position P1 and the second position P2, and the catheter assembly 10 can be downsized. Furthermore, because the support main body portion 102 is provided in a manner rotatable to the housing 19 by the axial rod portion 100, the support main body portion is smoothly displaced between the first position P1 and the second position P2. This enables easy switch between the supportable state for the catheter 12 and the detachable state for the catheter hub 14 and the like. Additionally, in the case where the side edge 46a of the catheter operation member 20 exists in the operation member groove portion 108, the support member 44 becomes unable to be rotated, and it is possible to continue making the support main body portion 102 stand by at the first position P1 capable of supporting the catheter 12. On the other hand, in the case where the cut-out portion 47 of the catheter operation member 20 exists in the operation member groove portion 108, the support member 44 becomes rotatable and the support main body portion 102 can be displaced to the second position P2 at which the catheter hub 14 and the like are allowed to pass.

Furthermore, at the time of advancing and retracting operation of the catheter operation member 20, the support main body portion 102 is elastically deformed and allows the holding portion 58 to pass even when the holding portion 58 holding the catheter 12 contact the same. Therefore, mobility of the catheter operation member 20 can be sufficiently secured. The catheter operation member 20 largely rotates the support main body portion 102 by contacting the contacting projection 120 at the time of advancement, and the support main body portion 102 can be surely arranged at the second position P2 from the first position P1. Therefore, unintended contact between the catheter operation member 20 and the support member 44 can be prevented at the time of retracting operation of the catheter operation member 20, and the catheter operation member 20 can be made to smoothly retract.

Note that the catheter assembly 10 according to the present invention is not limited to the above-described embodiment, and various kinds of application examples and modified examples are applicable. For example, the catheter assembly 10 may have a structure in which a guide wire not illustrated is housed in the through-hole 16b of the inner needle 16, and the guide wire is exposed from the needle tip 16a to guide the catheter 12 by controlling a guide wire operation member not illustrated and connected to the guide wire.

Furthermore, the support member 44 capable of supporting the catheter 12 inside the housing 19 is not limited to the above-described component, and for example, a slider (not illustrated) that slides between the first position P1 and the second position P2 may be applied instead of the support member 44. In this case, the slider is adapted to advance and retract in a width direction of the housing 19 (direction orthogonal to the moving direction of the catheter 12). With this structure, the slider can easily switch the position between the first position P1 capable of supporting the catheter 12 near the axial center of the housing 19 and the second position P2 at which the catheter hub 14 and the like are allowed to pass outside the housing 19.

First Modified Example

Next, a catheter assembly 10A according to a first modified example will be described. Note that a reference sign same as the one used in the above-described embodiment has the same structure or the same function in the following description, and a detailed description therefor will be omitted.

Figure 11:
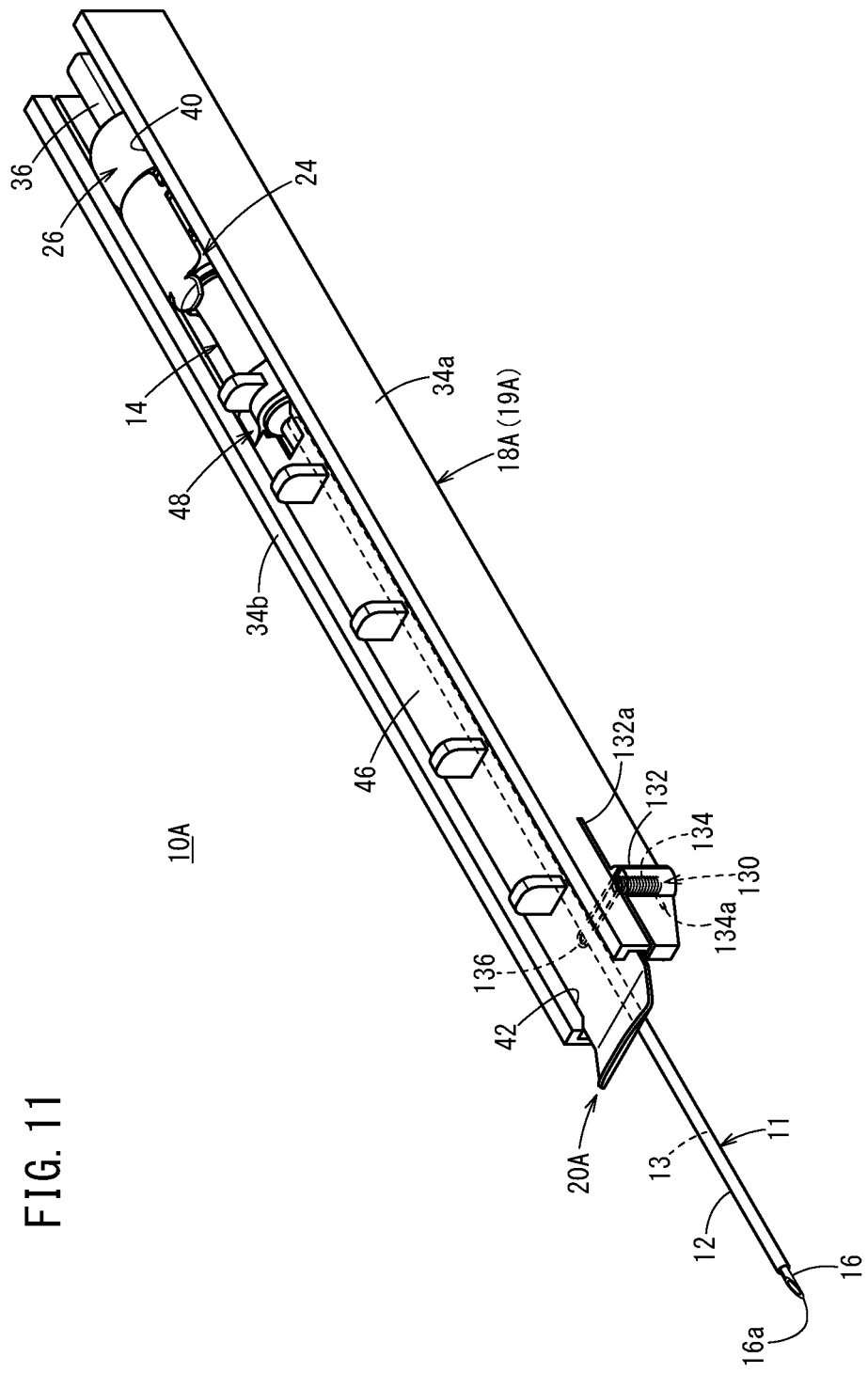
FIG. 11 is a perspective view illustrating an entire structure of a catheter assembly according to a first modified example.

A catheter assembly 10A according to the first modified example differs from the catheter assembly 10 in that a torsion spring 130 is adopted as the support member to support the catheter 12 as illustrated in FIG. 11. Furthermore, a needle hub 18A (housing 19A) of the catheter assembly 10A includes a housing portion 132 to arrange the torsion spring 130 instead of the above-described arrangement recessed portion 43.

The housing portion 132 slightly bulges outward in the width direction from the side wall 34a of the housing 19A and includes a spring housing chamber inside thereof (not illustrated). Furthermore, the housing portion 132 includes, on the lower side of the rail portion 42, a slit 132a capable of passing a support spring portion 136 when the support spring portion 136 of the later-described torsion spring 130 is displaced.

The torsion spring 130 includes: a coil portion 134 formed by winding a wire member made of a metallic material in a spiral form; and the support spring portion 136 (support main body portion, projecting portion) projecting from an upper end of the coil portion 134 in a lateral direction (direction orthogonal to an axial center of the coil portion 134). The coil portion 134 is assembled to the housing 19A such that the axial direction thereof is formed along a vertical direction of the housing 19A. Furthermore, the coil portion 134 includes a pin 134a projecting from a lower end portion, and the pin 134a is fixed to the housing portion 132 in a non-rotatable manner.

The support spring portion 136 is formed in a U-shape in a plane view, and extends from the coil portion 134 to a position exceeding the multiple tube unit 11 and the holding portion 58 (first position P1) in the state that the torsion spring 130 is assembled to the housing 19A. With this structure, the support spring portion 136 can support the multiple tube unit 11 and prevents the multiple tube unit 11 from being warped when the user operates a catheter operation member 20A. Because the support spring portion 136 is elastically deformed in the vertical direction by the coil portion 134 and own spring force of the support spring portion 136 itself, the support spring portion 136 escapes downward when contacted by the holding portion 58, and easily makes the holding portion 58 pass at the time of advancement and retraction of the catheter operation member 20A.

Figure 12A:
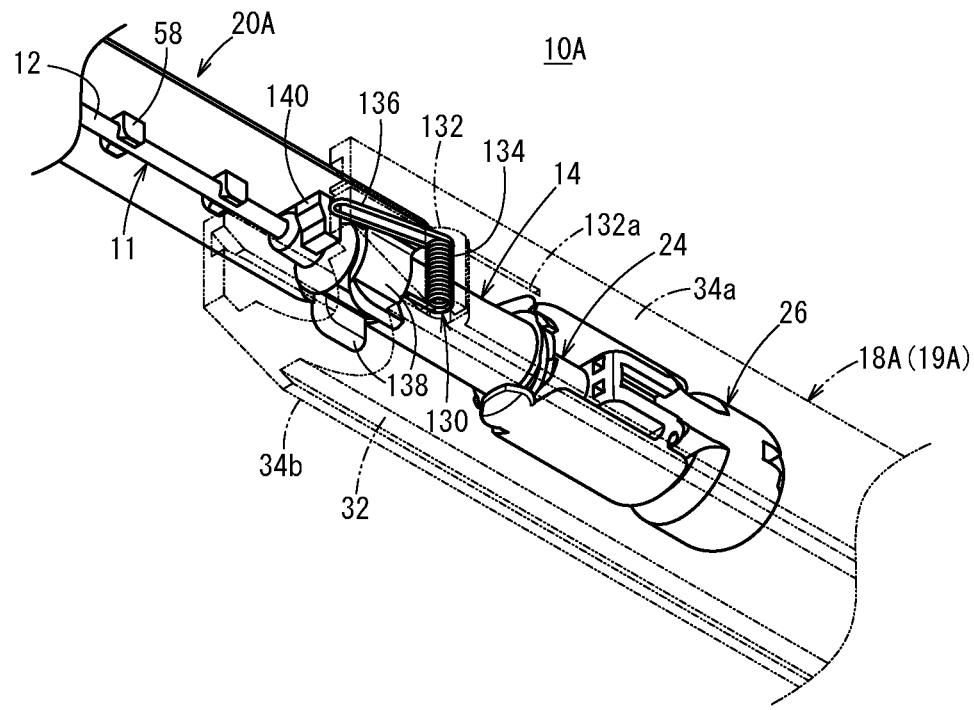
FIG. 12A is a perspective view illustrating a state in which a support spring portion is displaced to the second position when viewed from an obliquely lower side.

Furthermore, the hub attachment portion 48 of the catheter operation member 20A is formed of a pair of leg portions 138 adapted to clamp the outer peripheral surface of the catheter hub 14 as illustrated in FIG. 12A. Additionally, the catheter operation member 20A includes a block 140 projecting downward on a lower surface near the side edge 46a on a front side of the pair of leg portions 138. The support spring portion 136 is rotated anti-clockwise (elastically deformed) in a plane view by the block 140 contacting the support spring portion 136 along with advancement of the catheter operation member 20A. Therefore, the support spring portion 136 is displaced to a position (second position P2) at which the support spring portion 136 is inserted into the slit 132a on the distal end side, and allows the catheter hub 14, catheter hub auxiliary member hub 24, and needle protection member 26 to pass.

Figure 12B:
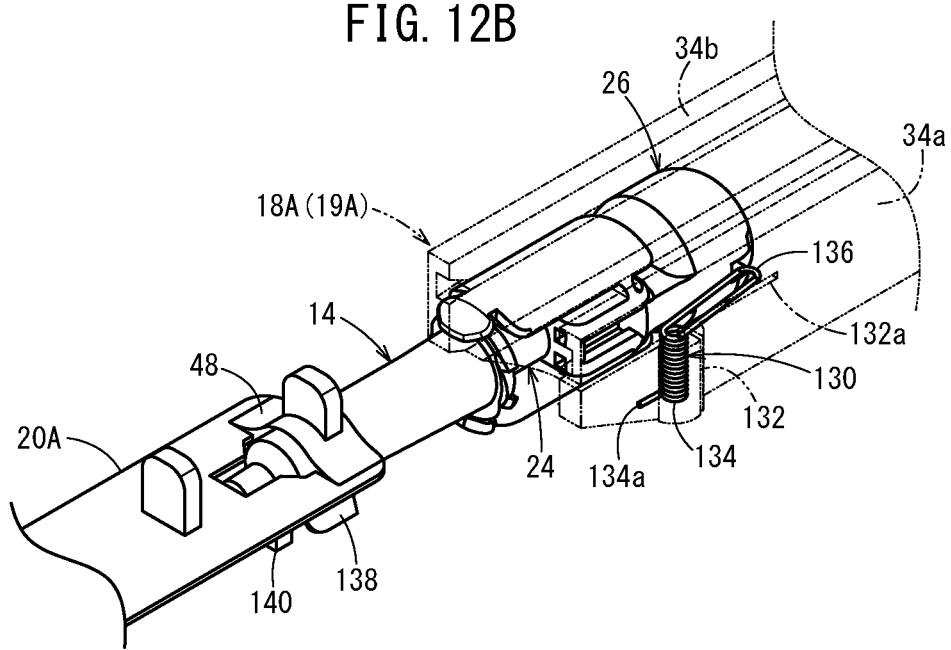
FIG. 12B is a perspective view illustrating a state in which a catheter hub, an auxiliary member hub, and a needle protection member retract in a proximal end direction when viewed from an obliquely upper side.

Furthermore, at the time of assembling the catheter operation member 20A to the housing 19A and when the catheter operation member 20A retracts again, the needle protection member 26 and the like contact the support spring portion 136 and rotates the support spring portion 136 in the proximal end direction as illustrated in FIG. 12B. Consequently, the support spring portion 136 is inserted into the slit 132a on the proximal end side, and allows the catheter hub 14, catheter hub auxiliary member hub 24, and needle protection member 26 to pass.

As described above, in the catheter assembly 10A according to the first modified example also, effects same as the catheter assemblies 10 can be obtained. Particularly, the torsion spring 130 can stably support the multiple tube unit 11 until the torsion spring 130 is pressed by the block 140, and the multiple tube unit 11 is effectively prevented from being warped. On the other hand, the torsion spring 130 can easily allow the catheter hub 14, auxiliary member hub 24, and needle protection member 26 to pass along with pressing by the block 140. Meanwhile, the above-described wing 116 and contacting projection 120 may be provided at the torsion spring 130.

Second Embodiment

Figure 13:
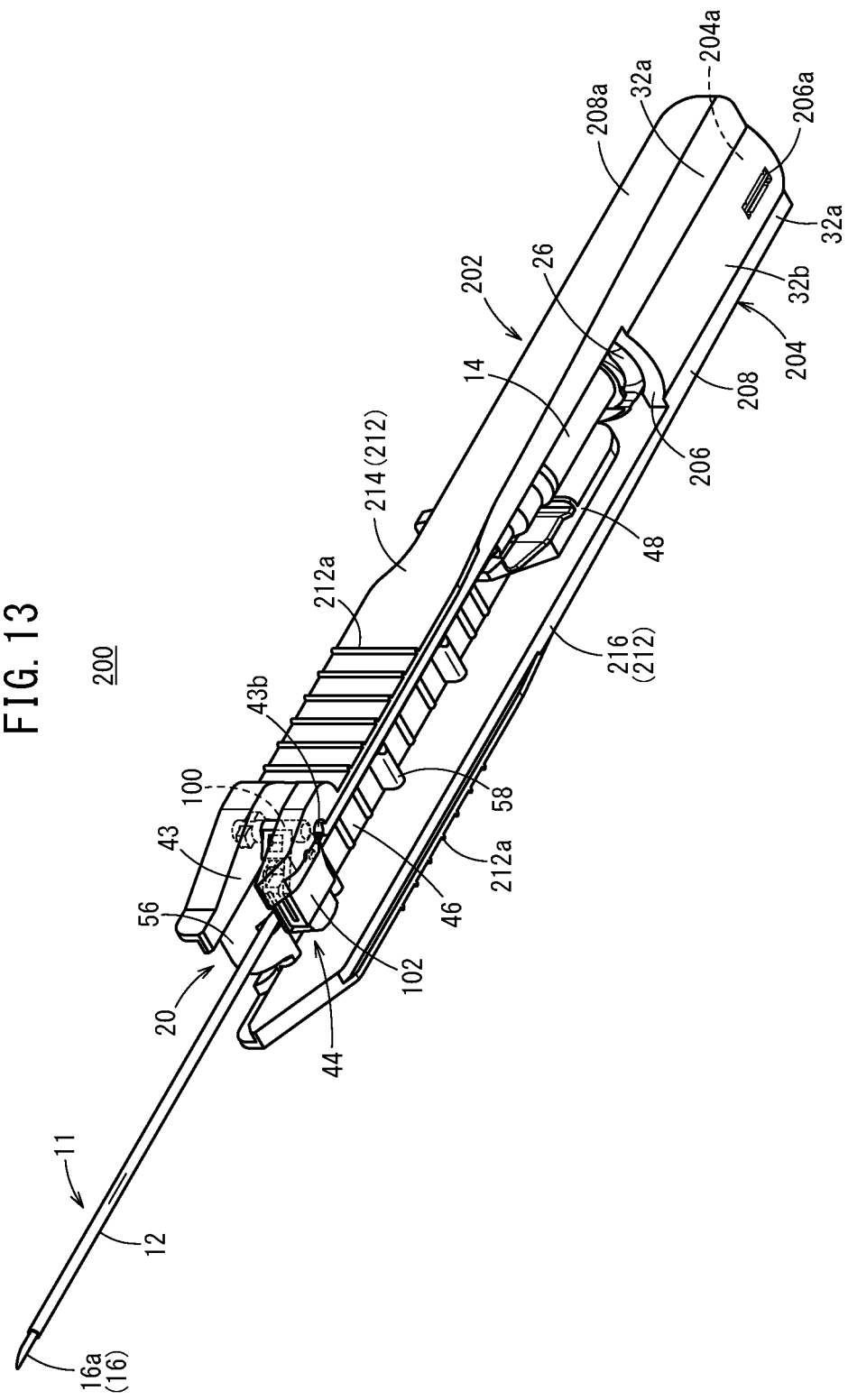
FIG. 13 is a perspective view illustrating an entire structure of a catheter assembly according to a second embodiment of the present invention.
Figure 14:
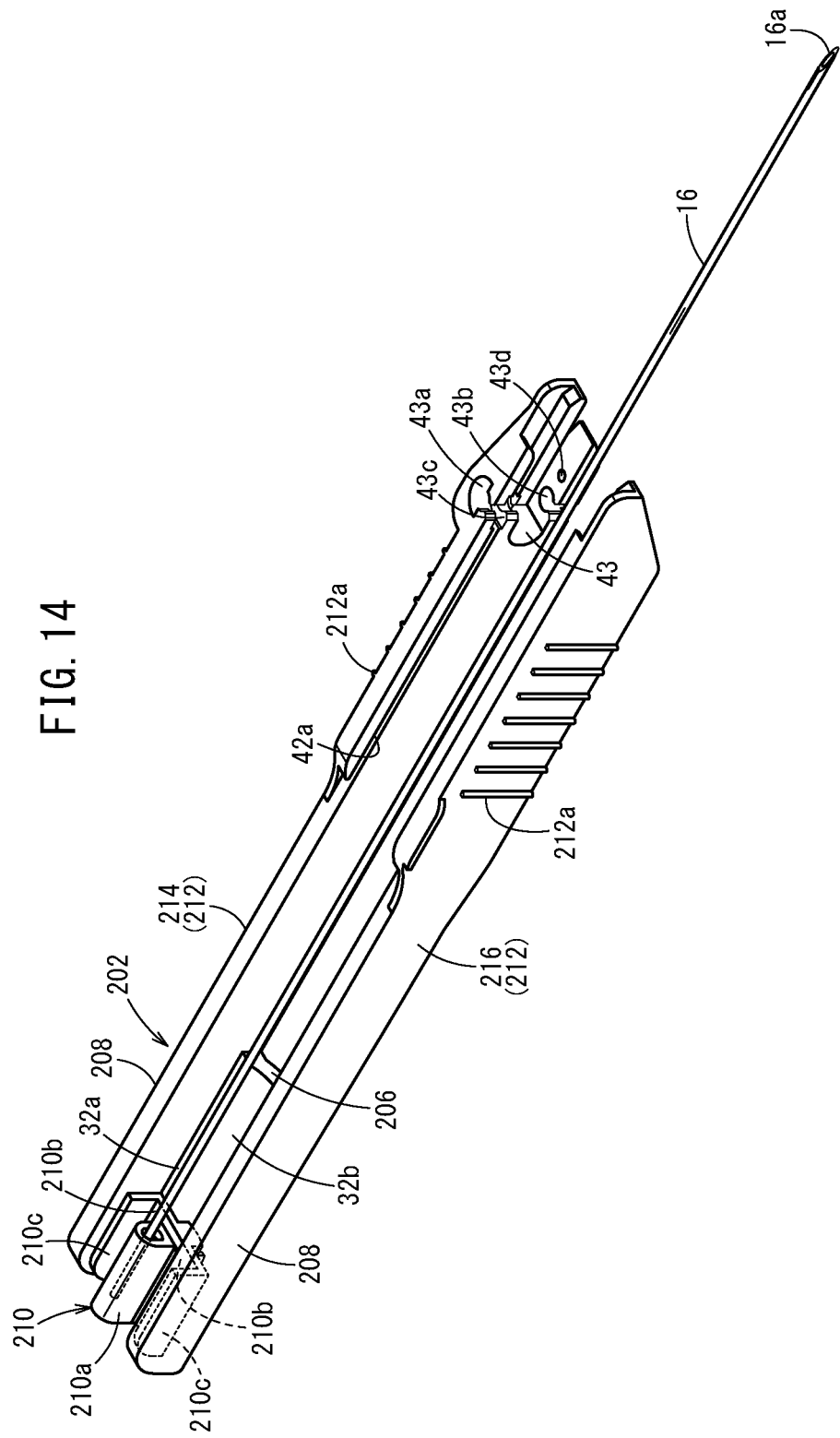
FIG. 14 is a perspective view illustrating a needle hub and an inner needle of the catheter assembly in FIG. 13.

Next, a catheter assembly 200 according to a second embodiment of the present invention will be described. In the catheter assembly 200, a shape of a needle hub 202 differs from a needle hub 18 of a catheter assembly 10 according to a first embodiment as illustrated in FIGS. 13 and 14. More specifically, the needle hub 202 includes a housing 204 and a pair of arms 212 projecting from the housing 204 in a distal end direction.

The housing 204 includes: a lower wall 206 having a pair of side portions 32a and a guide groove 32b; and a pair of side walls 208 projecting upward from both side portions of the lower wall 206, and forms a housing space 204a on an inner side of the lower wall 206 and the pair of side walls 208. A needle protection member 26 is housed in the housing space 204a of the housing 204 in the initial state. Meanwhile, the catheter assembly 200 does not include an auxiliary member 22 and an auxiliary member hub 24 described above, but needless to mention that the respective components may be also included.

Furthermore, as illustrated in FIG. 14, a needle holding member 210 formed as a separate body from the housing 204 is fixed more on a proximal end side than the needle protection member 26 on the lower wall 206 of the housing 204. The needle holding member 210 includes a holding base portion 210a at a center portion in a width direction, a horizontal plate 210b projecting outward in the width direction from the vicinity of a lower side of the holding base portion 210a and contacting the pair of side portions 32a, and a vertical plate 210c projecting upward from a projecting end of the horizontal plate 210b and contacting the pair of side walls 208. The holding base portion 210a fixes and holds a proximal end portion of an inner needle 16 at an upper portion thereof. Furthermore, a hook-like connecting portion not illustrated but adapted to hook an attachment hole 206a (refer to FIG. 13) of the lower wall 206 and firmly fix the needle holding member 210 to the housing 204 is provided at a lower portion of the holding base portion 210a.

As illustrated in FIGS. 13 and 14, the pair of arms 212 (first arm 214 and second arm 216) is connected to the pair of side walls 208 of the housing 204, and extend directly in a distal end direction. A rail portion 42 is provided at an inner surface of each of the pair of arms 212, and a grip 212a to be held by a user is provided on an outer surface of each of the arms. Furthermore, same as the first embodiment, in the first arm 214, an arrangement recessed portion 43, a pair of bearing holes 43a, 43b, a window 43c, and a locking recessed portion 43d are formed, and a support member 44 is rotatably attached. Meanwhile, the pair of arms 212 may be formed of a metallic material in order to enhance rigidity (more specifically, to enhance an extending posture), or an enhancement member such as a metal bar (not illustrated) may be embedded in the inside made of a resin material.

In the catheter assembly 200 according to the second embodiment, effects same as the catheter assembly 10 can be obtained. More specifically, by supporting a lower side of the multiple tube unit 11 with the support member 44 attached to the needle hub 202, a multiple tube unit 11 can be properly prevented from being warped at the time of puncture. On the other hand, because the needle hub 202 includes the pair of arms 212, weight reduction of an entire assembly is achieved, and also mobility of a catheter operation member 20 is improved by reducing friction at the time of advancement and retraction of the catheter operation member 20.

Second Modified Example

Figure 15:
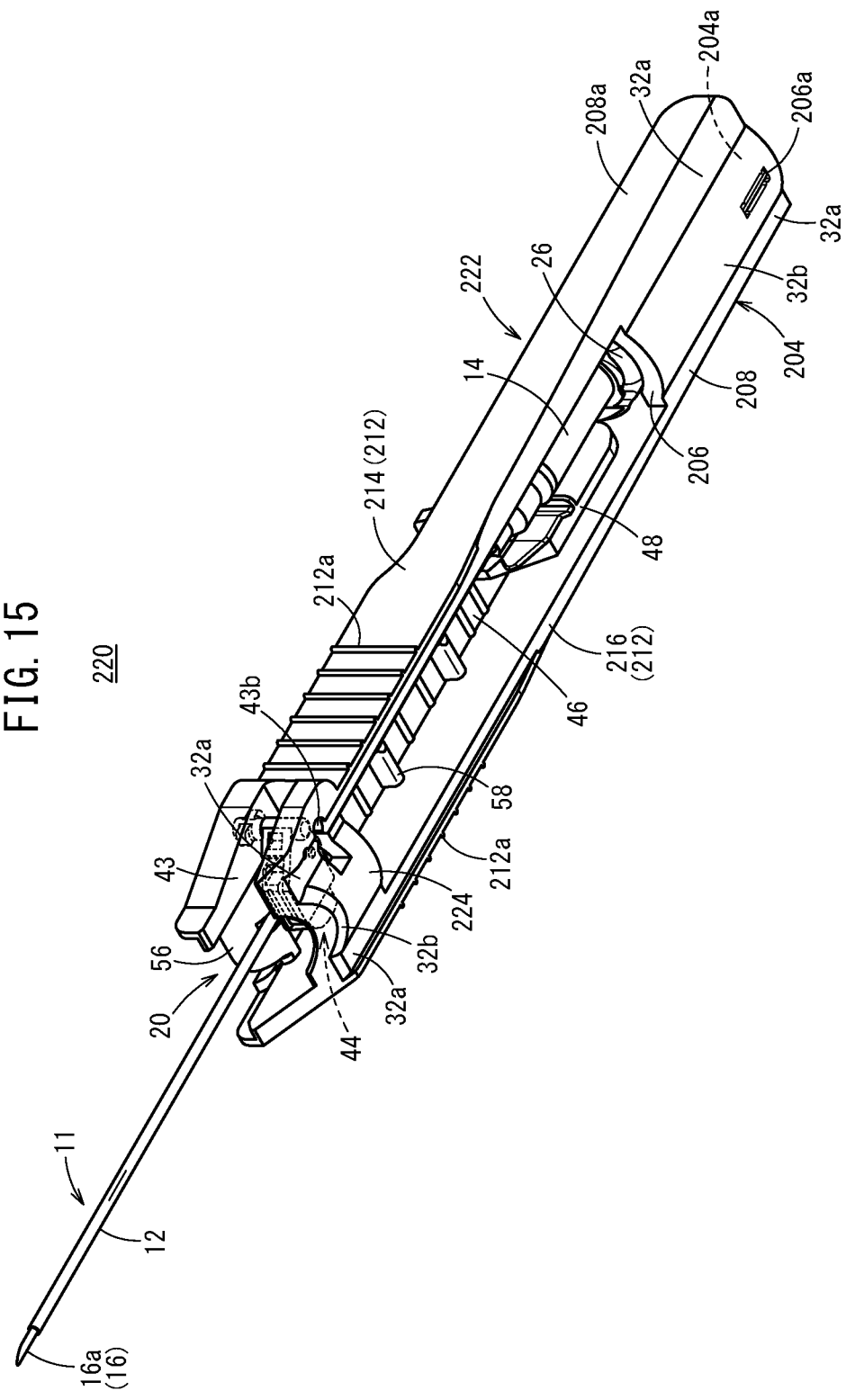
FIG. 15 is a perspective view illustrating an entire structure of a catheter assembly according to a second modified example.

Furthermore, a catheter assembly 220 (needle hub 222) according to a second modified example illustrated in FIG. 15 includes the pair of arms 212 same as the needle hub 202 according to the second embodiment but has a structure further including a connection bridge portion 224 to provide a bridge between the pair of the arms 212. The connection bridge portion 224 is integrally formed with the pair of arms 212 on an inner surface at a lower position on a distal end sides of the pair of arms 212. The connection bridge portion 224 has a length in a width direction of the lower wall 206 of the housing 204 and includes a pair of side portions 32a and a groove portion 32b. Furthermore, an axial length of the connection bridge portion 224 corresponds to an installation area of the support member 44, and the connection bridge portion is set so as not to expose a lower side of the support member 44.

Thus, because the needle hub 222 includes the connection bridge portion 224 on the distal end sides of the pair of arms 212, an interval on the distal end side and an entire portion of the pair of arms 212 can be set constant. Therefore, even when the user grips the vicinity of the grip 212a of the pair of the arms 212, a shape of the needle hub 222 can be properly maintained and advancing and retracting operation of the catheter operation member 20 can be smoothly performed.

Third Modified Example

Figure 16:
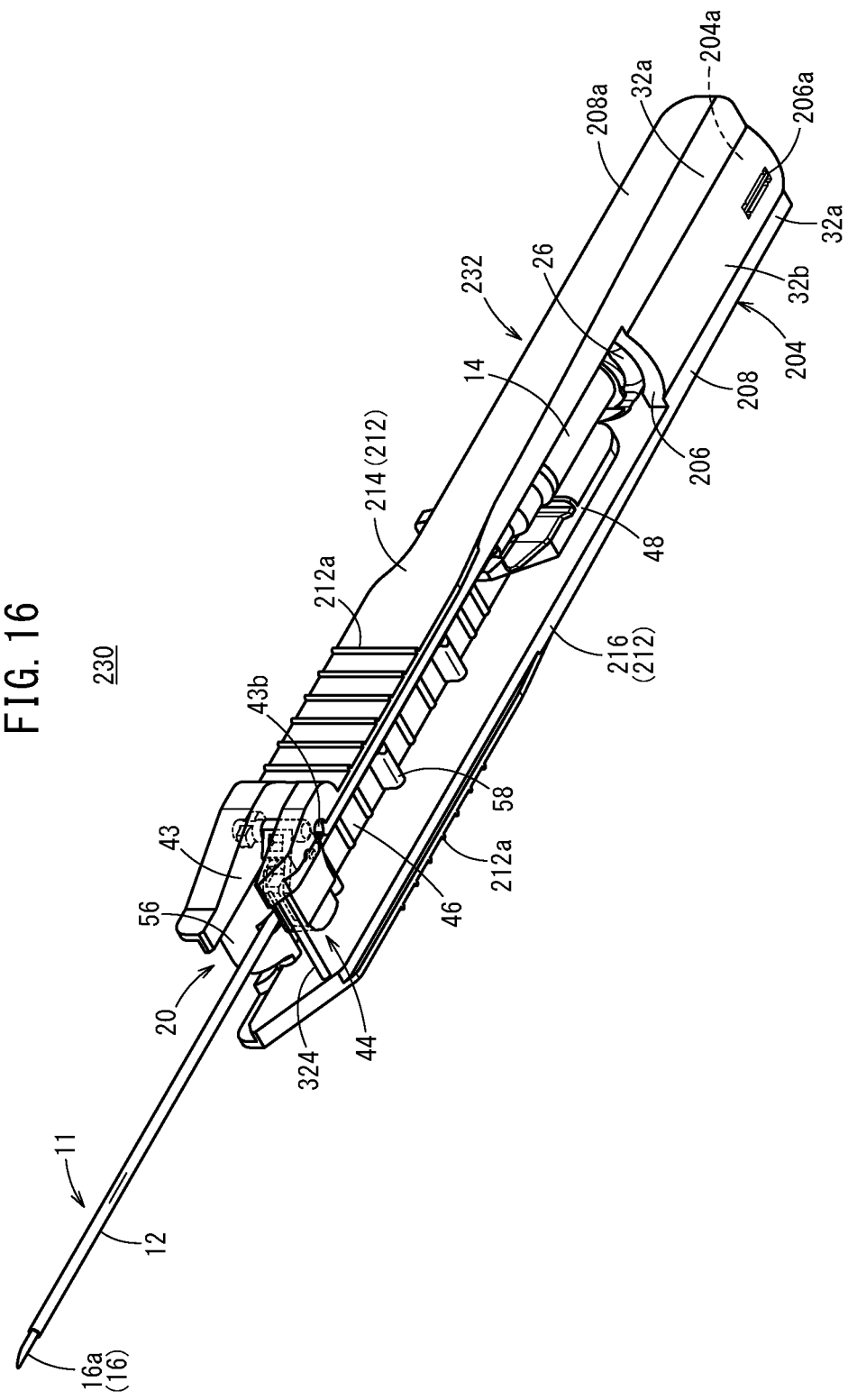
FIG. 16 is a perspective view illustrating an entire structure of a catheter assembly according to a third modified example.

Furthermore, a catheter assembly 230 (needle hub 232) according to a third modified example illustrated in FIG. 16 has a structure including a connection rod 324 to connect the distal end sides of the pair of arms 212 instead of the above-described connection bridge portion 224. The connection rod 324 is a member made of, for example, a metallic material and formed a shape of a cylindrical rod. The connection rod 324 provides a bridge having a length in a width direction of the lower wall 206 between the pair of arms 212 in the same manner as the connection bridge portion 224, thereby making the interval between the pair of arms 212 constant.

In short, the needle hubs 222, 232 can adopt various kinds of structures which enhance the extending posture of the pair of arms 212 and smoothens mobility of the catheter operation member 20. For example, the connection bridge portion 224 and the connection rod 324 are provided at not only the distal end sides of the pair of arms 212 but also middle positions in the extending directions of the pair of arms 212.

What is claimed is:
1. A catheter assembly comprising:
a hollow catheter;
a catheter hub to which the catheter is fixed;

an inner needle including a needle tip, the inner needle being detachably disposed inside of the catheter;
a needle hub to which the inner needle is fixed;
a catheter operation member configured to move the catheter relative to the inner needle; and
a support member disposed at the needle hub,
wherein the support member includes a support main body portion that is movable relative to the needle hub between (i) a first position at which, in a direction perpendicular to a longitudinal axis of the catheter, the catheter is interposed between the support member and the catheter operation member, and the support main body portion contacts and supports the catheter, and (ii) a second position that is a different position from the first position, at which the support main body portion does not contact the catheter.

2. The catheter assembly according to claim 1, wherein, when the catheter assembly is in an initial state in which the needle tip projects from a distal end of the catheter, the catheter is supported by being interposed between the catheter operation member and the support member.

3. The catheter assembly according to claim 1, wherein:
when the catheter assembly is in an initial state in which the needle tip projects from a distal end of the catheter, the support main body portion of the support member is inhibited from being moved from the first position, and
when the catheter operation member is advanced relative to the needle hub, the support main body portion is released from inhibition of movement from the first position.

4. The catheter assembly according to claim 1, wherein the catheter operation member includes a holding portion configured to directly hold the catheter in a detachable manner.

5. The catheter assembly according to claim 1, wherein the support member is rotatably attached to the needle hub.

6. The catheter assembly according to claim 5, wherein the support member includes an axial rod portion rotatably attached to the needle hub, and the support main body portion projects in a direction orthogonal to an axial direction of the axial rod portion.

7. The catheter assembly according to claim 6, wherein:
the needle hub includes a groove-like rail portion,
the axial rod portion includes a groove portion arranged in the rail portion, and
the catheter operation member includes:
a side edge housed in the rail portion and the groove portion in a slidable manner, the side edge being configured to be guided at a time of relative movement of the catheter operation member with respect to the needle hub, and
a cut-out portion not housed in the rail portion and the groove portion, the cut-out portion being formed by cutting out the side edge at a position at or near an attachment position to the catheter hub.

8. The catheter assembly according to claim 7, wherein the axial rod portion includes a cam portion, and the groove portion extends from a first end of the cam portion to a second end of the cam portion.

9. The catheter assembly according to claim 6, wherein the support main body portion includes a projection configured to contact a proximal end portion of the catheter operation member and displace the support main body portion from the first position to the second position along with advancement of the catheter operation member.

10. The catheter assembly according to claim 4, wherein the support member is rotatable about an axis that is transverse to a longitudinal axis of the needle hub.

11. The catheter assembly according to claim 1, wherein the support member is a torsion spring including a coil portion formed by winding a wire member, and a projecting portion formed as the support main body portion and projecting radially outward from the coil portion.

12. The catheter assembly according to claim 1, wherein the support main body portion is elastically deformed in a direction orthogonal to a moving direction of the catheter.

13. The catheter assembly according to claim 1, wherein, when the support main body portion is in the first position, the support main body portion is inclined downward and outward in a width direction of the needle hub from a portion that contacts and supports the catheter.

14. A catheter assembly comprising:
a hollow catheter;
a catheter hub to which the catheter is fixed;
an inner needle including a needle tip, the inner needle being detachably disposed inside of the catheter;
a needle hub to which the inner needle is fixed;
a catheter operation member configured to move the catheter relative to the inner needle; and
a support member disposed at the needle hub,
wherein the support member includes a support main body portion that is movable relative to the needle hub between (i) a first position at which the support main body portion contacts and supports the catheter, and (ii) a second position that is a different position from the first position, at which the support main body portion does not contact the catheter,
wherein the support member is rotatably attached to the needle hub, and
wherein the support member includes an axial rod portion rotatably attached to the needle hub, and the support main body portion projects in a direction orthogonal to an axial direction of the axial rod portion.

15. The catheter assembly according to claim 14, wherein, when the catheter assembly is in an initial state in which the needle tip projects from a distal end of the catheter, the catheter is supported by being interposed between the catheter operation member and the support member.

16. The catheter assembly according to claim 14, wherein:
when the catheter assembly is in an initial state in which the needle tip projects from a distal end of the catheter, the support main body portion of the support member is inhibited from being moved from the first position, and
when the catheter operation member is advanced relative to the needle hub, the support main body portion is released from inhibition of movement from the first position.

17. The catheter assembly according to claim 14, wherein the catheter operation member includes a holding portion configured to directly hold the catheter in a detachable manner.

18. The catheter assembly according to claim 14, wherein the support member is rotatable about an axis that is transverse to a longitudinal axis of the needle hub.

* * * * *